United States Patent [19]
Brill

[11] Patent Number: 5,435,324
[45] Date of Patent: Jul. 25, 1995

[54] APPARATUS FOR MEASURING PSYCHOTHERAPY OUTCOMES

[75] Inventor: Peter L. Brill, Radnor, Pa.

[73] Assignee: Compass Information Services, Inc., Radnor, Pa.

[21] Appl. No.: 249,100

[22] Filed: May 25, 1994

Related U.S. Application Data

[63] Continuation of Ser. No. 934,390, Aug. 21, 1992, abandoned.

[51] Int. Cl.$^6$ ............................................. A61B 17/00
[52] U.S. Cl. .................................................. 128/897
[58] Field of Search ............................... 128/731–732, 128/897–898; 364/413.01

[56] References Cited
U.S. PATENT DOCUMENTS 4,699,153  10/1987  Shevrin et al. .................. 128/731

*Primary Examiner*—Angela D. Sykes
*Attorney, Agent, or Firm*—Reed, Smith, Shaw & McClay

[57] ABSTRACT

A method and apparatus for measuring a patient's psychotherapy progress is provided. Initial patient mental health is measured by administering a questionnaire measuring three psychological variables. The three psychological variable measures are combined into a mental health index. Following a number of sessions of psychotherapy, the patient's subsequent psychological condition is again measured using the three psychological variables. Patient session records are stored in a large database. Patient progress can thus be compared versus patient initial psychological condition, typical patient outcomes as stored in the database, and patient improvement as a function of a number of sessions of psychotherapy can be determined. The system further provides a case manager with a measure of the effectiveness of continued psychotherapy sessions, and a basis of comparison of various psychotherapy providers.

2 Claims, 10 Drawing Sheets

PATIENT 30075—PERCENTILE RANKS

| SCORE | INTAKE | SESSION 77 | CHANGE |
|---|---|---|---|
| WELLBEING | 90 | 90 | 0 |
| SYMPTOMS | | | |
| HOSTILITY | 3 | 10 | 7 |
| INTERPERSONAL SENSITIVITY | 16 | 16 | 0 |
| DEPRESSION | 7 | 7 | 0 |
| PARANOIA | 4 | 8 | 4 |
| OBSESSIVE | 11 | 18 | 7 |
| ANXIETY | 7 | 19 | 12 |
| SLEEP DISTURBANCE | 6 | 19 | 13 |
| | 10 | 40 | 30 |
| FUNCTIONING | | | |
| WORK | 92 | 81 | -11 |
| HEALTH | 70 | 90 | 20 |
| SELF-MANAGEMENT | 84 | 84 | 0 |
| SOCIAL RELATIONSHIPS | 90 | 86 | -4 |
| INTIMATE RELATIONSHIPS | 75 | 40 | -35 |
| FAMILY FUNCTIONING | 95 | 56 | -39 |
| | 86 | 27 | -59 |

FIG. 11

APPARATUS FOR MEASURING PSYCHOTHERAPY OUTCOMES

This application is a continuation of U.S. patent application Ser. No. 07/934,390, filed Aug. 21, 1992, now abandoned.

BACKGROUND OF THE INVENTION

This invention relates to psychotherapy. More particularly, this invention relates to a system for measuring and quantifying a patient's psychological condition and the progress, stasis, or retrogression thereof, and for administering pyschotherapy based on such measurements.

Costs in the health care field have grown at an alarming rate. Efforts to contain these costs through devices such as DRGs have slowed the growth of inpatient care, but total health care costs continue to escalate as the inpatient cost savings have shifted into expenditures for outpatient treatment. Meanwhile, the cost of mental health treatment has greatly outpaced general health care costs. Prior cost containment efforts have focused on inpatient costs. A case management approach has been applied to cost containment efforts. Often, much of a company's mental health costs are for inpatient treatment. However, recent trends are forcing a shift toward outpatient care. Furthermore, simply decreasing the amount of mental health coverage is not an attractive alternative, since poorly treated employees typically work less effectively and have increased absenteeism. Moreover, the families of such employees typically use the general health care system at an increased rate.

Mental health care may be characterized by two characteristics of overriding importance: the cost of the care, and the results or benefits of the care. Although cost is easily measured, treatment outcomes and the benefits of mental health care have been difficult if not impossible to measure. Accordingly, efforts to improve the system for delivering mental health care have focused on cost, the only measured variable in the system. Since the cost parameter can be measured, systems which minimize cost tend to be rewarded without regard to the unknown effect of cost minimizing measures on patient care. Efforts to control costs include restricting access to mental health care; a case manager may encourage providers to deny care altogether or to terminate care as early as possible. However, without a reasonably accurate and objective method of evaluating cases, a case manager or other interested person is unable to rationally allocate the limited resources for psychotherapy among those who demand it. For instance, extensive resources may be allocated to patients who would show limited or no improvement even after extended treatment, while resources may be denied to patients who would show substantial improvement with limited treatment. Moreover, without such a method the case manager or other interested person cannot rationally determine which providers should be engaged to provide the most cost-effective and appropriate treatment in an individual case or on an overall basis. Lacking an ability to measure psychotherapy outcomes, efforts to select a provider and a course of therapy have focused on process measures, i.e. measures which attempt to infer the effect of therapy from characteristics of the therapy process such as the credentials of the provider. Too often the therapy approved and provided to a patient is made to fit the insurance or other benefits available to the patient, rather than the patient's condition. In contrast, in physical health care there are numerous lab tests which can accurately diagnose a physical illness and may be used to determine patient response, individually or on a group statistical basis, to particular courses of medical or surgical treatment. Although physical health care costs have continued to rise, the availability of such tests and outcome measures have enabled case managers in that field to more rationally determine when a treatment is necessary or appropriate for a condition and allocate limited physical health care resources.

SUMMARY OF THE INVENTION

It is therefore a general object of the invention to provide an objective and reliable method and apparatus ("system") for measuring the psychological condition of a person.

It is a further object of the invention to provide a system for measuring the outcome of psychotherapy, i.e. its effect upon the psychological condition of a person.

It is a further object of the invention to provide a system for administering psychotherapy using measurements of psychological condition to initially determine, and as feedback to monitor and control, the course of psychotherapy provided to a person.

It is a further object of the invention to provide a system for evaluating the relative effectiveness of psychotherapy providers.

The present invention provides an apparatus and a method for measuring a patient's psychological condition and changes therein. The method preferably provides a single number indicative of a person's overall psychological condition, as well as single numbers indicative of a person's psychological condition with respect to each psychological variable involved in the measurement. The invention further includes various methods of administering psychotherapy based on such measurements.

One such method is for feedback control of providing psychotherapy to a patient and includes the steps of measuring the patient's initial psychological condition with respect one or more psychological variables, and preferably three specific variables; administering a dose of psychotherapy; measuring the patient's subsequent psychological condition with respect to the measured psychological variables; and comparing the subsequent measurement with the initial measurement to determine the patient's progress. These steps may be repeated, using measured information to appropriately modify the psychotherapy provided in subsequent doses, until measurements indicate that further psychotherapy is not needed because the patient's psychological condition is acceptable or that further psychotherapy is unjustifiable because significant improvement is not expected or the expected benefit of further treatment cannot be justified by its expected cost.

Another such method is to evaluate the relative effectiveness of psychotherapy providers, including individual therapists and/or organizations which provide or pay for psychotherapy services. In accordance with this method, the effectiveness of such providers may be determined based upon measurements of the psychological condition of the patients to whom they provide psychotherapy. For instance, improvement of psychological condition per dose of psychotherapy may be computed as a figure of merit indicating effectiveness.

In accordance with the invention, measurement of psychological condition is based upon tests. Preferably, such tests are administered to a patient by obtaining responses to a set of standardized questions. It is particularly preferred to obtain self-reporting responses of the patient as well as responses indicating a clinician's professional evaluation of the patient.

The apparatus of the invention provides means for recording responses to a psychological test, preferably the patient's self-reported responses as well as a clinician's professional evaluation; a processor for calculating measures of the patient's psychological condition with respect to one or more psychological variables from the recorded responses, and preferably also for calculating a single-valued mental health index and clinical assessment index derived from the measured psychological variables; means for storing psychotherapy session records for a number of psychotherapy sessions, and preferably also for storing benchmark measures of the psychological variables; and means for determining a particular patient's progress by comparing measurements of the patient's psychological condition taken at different times. Preferably the apparatus includes a database of responses recorded with respect to many different patients, means for establishing and modifying the benchmarks based on the contents of the database, and means for determining a patient's expected progress from the patient session records and the database.

BRIEF DESCRIPTION OF THE DRAWINGS

The above and other objects, features, and advantages of the invention will become apparent on consideration of the following detailed description, taken in conjunction with the accompanying drawings, in which like reference characters refer to like parts throughout and in which:

FIG. 7 is a flow diagram illustrating a method for administering psychotherapy utilizing measurements obtained in accordance with the invention;

FIG. 11 is a listing of the example patient's percentile ranking with respect to certain psychological variables;

DETAILED DESCRIPTION OF THE INVENTION

Figure 1:
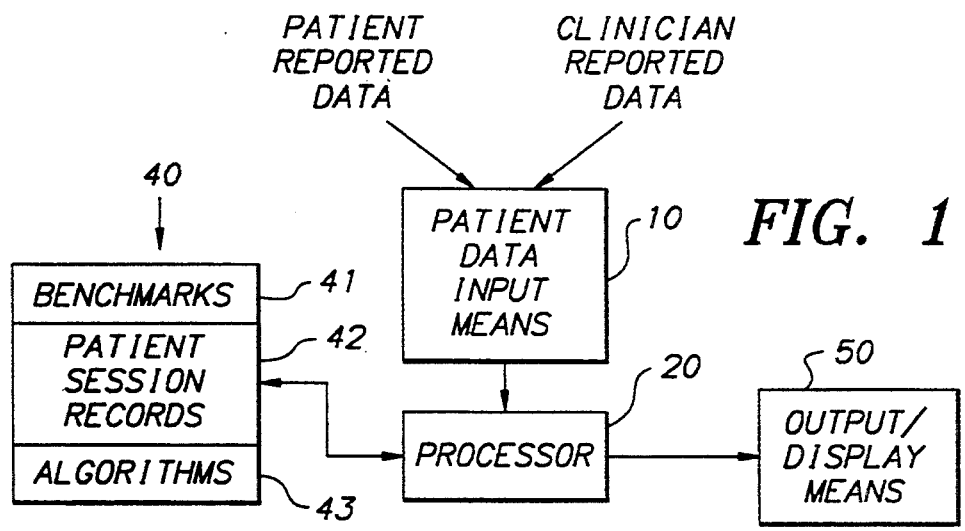
FIG. 1 is a block diagram of an apparatus in accordance with the invention.

The present invention provides an apparatus and method for providing standardized replicable measurements of psychological condition and psychotherapy outcomes for patients. The system quantifies psychological condition and progress, stasis or retrogression thereof by means of a psychological test which determines a person's condition with respect to one or more psychological variables. Test results for individuals are collected and stored in a computer database. As the amount of data in the database grows, self-validating and increasingly more reliable scales may be created to compare the progress of a particular patient with the progress of patients generally, and to compare the relative success or cost effectiveness of various therapy providers. The data are combined using algorithms to create numerical measures of psychological condition and the outcome of treatment. Measurements taken at the outset and at successive intervals during psychotherapy provide finite measures of the patient's ability to deal with problems, both perceived and real, and changes therein due to therapy. In accordance with the preferred embodiment of the invention, the psychological test of a patient includes self-reported responses of a patient to a standard patient questionnaire as well as a clinician's professional evaluation of the patient provided in response to a standard clinician questionnaire. Further in accordance with the preferred embodiment, the test provides responses indicative of the patient's condition with respect to a plurality of psychological variables. Such variables desirably include one or more of the following: subjective well-being; symptomatic distress; current life functioning; self-esteem; coping; temperament; and attitude. Applicant prefers to measure psychological condition with respect to three of these psychological variables: subjective well-being, symptomatic distress, and current life functioning. Subjective well-being is a measure of the patient's conception of contentment. Subjective well-being includes dimensions of distress, energy and health, emotional and psychological adjustment, and current life satisfaction. Symptomatic distress includes the psychological diagnoses of adjustment disorder, anxiety, bipolar disorder, depression, obsessive-compulsive disorder, phobia, and substance use disorders. Current life functioning includes dimensions of family functioning, health and grooming, intimate relationships, self-management, social relationships, and work functioning.

Patient responses to a questionnaire are used to assess the psychological variables for each patient. Applicant's presently preferred questionnaire is included in Appendix A to this application, "Outpatient Therapy Effectiveness Tracking System", and includes 11 questions directed to subjective well-being, 40 questions directed to symptomatic distress, and 24 questions directed to current life functioning, as well as questions directed to other areas. An analysis of this questionnaire is provided in Appendix B to this application, "The Howard Outpatient Tracking System". The questionnaire may be administered in the form of a test booklet, with the answers recorded on paper, or in the form of an interactive computer program, or by other suitable means. Applicant prefers to record responses on paper forms and input the response information into a computer by optically scanning the forms.

Applicant prefers to obtain a clinician's professional evaluation of a patient with respect to two psychological variables: a global assessment of psychopathology, and an assessment of the patient's current life functioning. The global psychopathology assessment scale may be taken from Axis V of the DSM-III-R as an overall rating of the patient's lowest level of current functioning using ten ten-point intervals. The life functioning assessment may be made with respect to life functioning scales ranging from 0 to 100 which separately assess the patient's functioning in the areas of family functioning, health and grooming, intimate relationships, self-management, social relationships, and work functioning, as set forth above. A preferred clinician questionnaire for obtaining these measurements is included in Appendix A, and an analysis of the questionnaire is included in Appendix B.

While the questionnaires set forth and described in Appendices A and B are presently preferred, other questionnaires suitable for use in the invention may already exist or may be devised.

Responses to the questionnaires, whether by the patient or the clinician, are used to compute single-valued quantities as psychological measures of the patient. Patient responses may be used to compute scaled scores with respect to each measured variable as psychological measures. They may also be used to compute as a psychological measure a single number indicative of the patient's overall psychological condition, which Applicant refers to as a "mental health index" or MHI. Likewise, the clinician's responses may be used to compute scaled scores with respect to each variable evaluated as well as a single-valued "clinical assessment index" or CAI as psychological measures.

Figure 2:
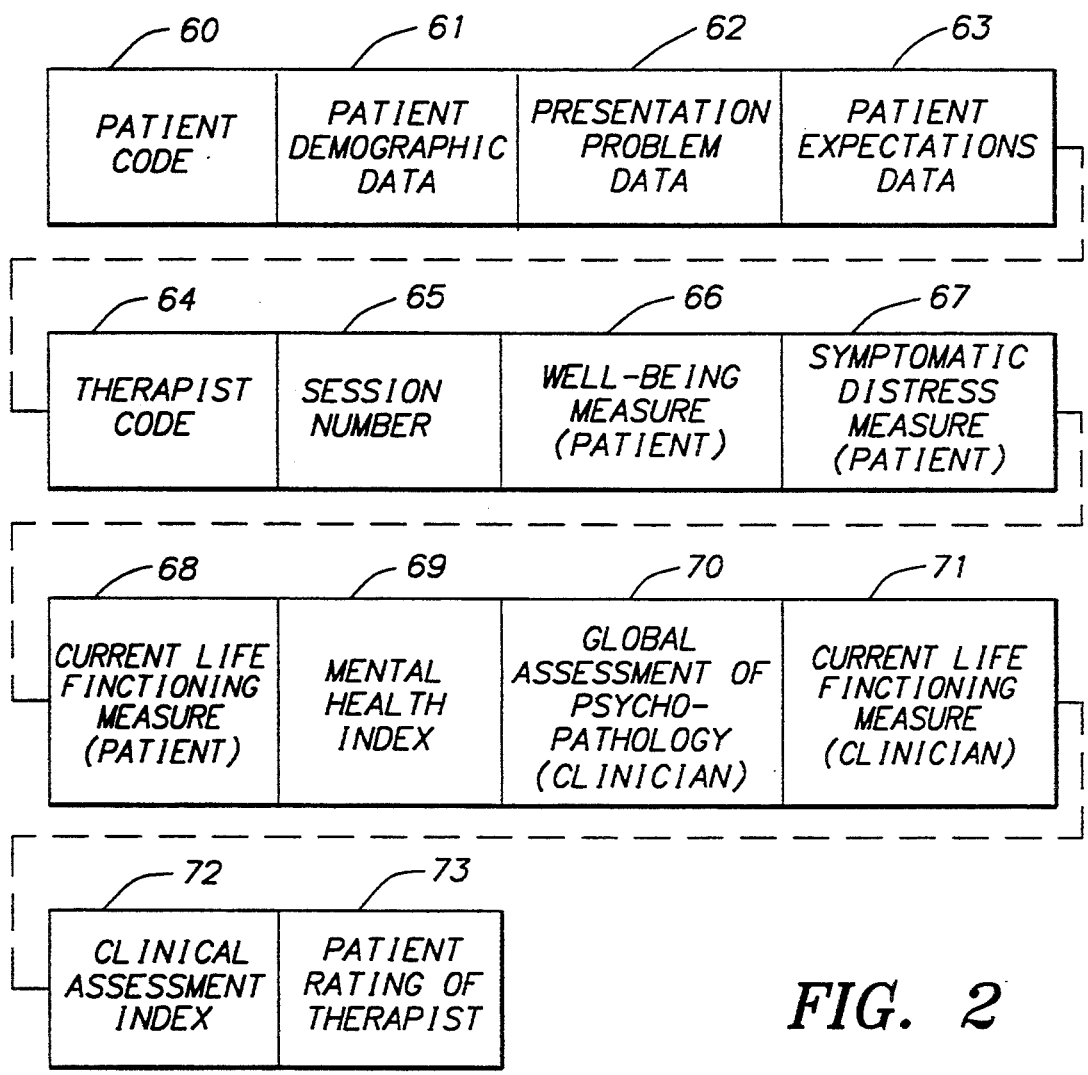
FIG. 2 is a block diagram illustrating the structure of a patient session record which may be stored in the apparatus.

FIG. 1 shows an exemplary embodiment of an apparatus for practicing the present invention. An input means 10 is used to input patient related data, preferably data from both patient and clinician responses from their respective questionnaires, to a memory 40 by means of a processor 20. Memory 40 includes patient session records 42, preferably structured as a database, algorithms 43 for computations including computations of psychological condition with respect to the raw data, and preferably also data representing benchmark values 41. A typical patient session record is illustrated in FIG. 2. Patient session record 42, in a preferred embodiment, comprises fields for data representing patient code 60 identifying the patient to which the record pertains; patient demographic data 61 such as age, gender, and education; presentation problem data 62; patient expectation data 63; therapist code 64 identifying the therapist; session number code 65 indicating the number of sessions that the patient has attended; well-being measure 66 derived from patient responses; symptomatic distress measure 67 derived from patient responses; current life function measure 68 derived from patient responses; mental health index 69 calculated based upon the patient well-being, symptomatic distress, and current life-function measures; data 70 representing the clinician's global assessment of psychopathology; a current life-function measure 71 derived from clinician responses; and a clinical assessment index 72 computed based upon the clinician's global assessment of psychopathology 70 and current life-function measure 71.

The records in the database also desirably include a field for data 73 representing the patient's perception of the therapist and the patient-therapist relationship.

With respect to the preferred questionnaires of Appendix A, the patient demographic data 61 may be derived from responses to the Personal Information questions; the presentation problem data 62 may be derived from responses to the Presenting Problems questions; the patient expectation data 63 may be derived from responses to the Treatment Needs and Expectations questions; the current well-being measure 66 may be derived from responses to the Current Well-Being questions; the symptomatic distress measure 67 may be derived from the Current Symptoms questions; the current life functioning measure 68 may be derived from responses to the Current Life Functioning questions; the clinician data 71 and 72 may be derived from responses recorded on the Clinician Form; and data 73 representing the patient's rating of the therapist may be derived from responses to the Therapist Ratings questions.

The data in the patient records 42 may be organized in a variety of fashions. For instance, instead of single records containing all of the data, constant data for a patient may be stored in one set of records and varying data for the patient may be stored in another set of records. Thus, constant data such as patient demographic data, presentation problems, and treatment expectations may be stored in one set of records, and the potentially variable data involved in the mental health and clinical assessment indices may be stored in separate sets of records for each test. In accordance with such data organization, and as illustrated in Appendix A, separate sets of questionnaires may be provided for initial or intake data and for data obtained during the course of therapy.

Several options are available for storing data relating to psychological condition. Regarding the patient-reported data, the raw data from the patient responses to the well being, symptomatic distress, and current life functioning questions may be stored; and/or psychological measures comprising single valued quantities representing the patient's condition with respect to each such variable may be computed according to an algorithm 43 and stored. Storage of the raw data is preferred to facilitate computation of revised single-valued quantities if the computation algorithms are changed, for instance upon revision of the questionnaires; while Applicant prefers to store computed psychological measures, whether or not the computed quantities are stored will depend on the user's evaluation of the utility of having computed quantities stored for immediate use without computation versus the cost of the additional storage required and necessity for updating the computed data in the database upon changes in the computation algorithms. Likewise, the single-valued quantities based on the clinician response may be computed and stored, or may not be stored and instead computed when needed; the same is true for the composite mental health index and clinical assessment index psychological measures.

The apparatus of FIG. 1 also includes an output means 50, which can be a video display terminal, printer, and/or other suitable means. The output device displays, prints, transmits, or otherwise communicates information derived from the database or the input data in a desired format. Such formats may include data listings, charts or graphs of computed quantities, and the like. Patient response input means 10 can be a terminal, or a magnetic tape reader, a disk drive or other suitable input means instead of or in addition to the preferred optical scanner input device.

Processor 20 operates on data relating to a test of a patient which has been input via input means 10 in accordance with algorithms 43 to produce single valued computed quantities with respect to each of the psychological variables tested and overall indices of mental health and clinical assessment. Such algorithms will generally include scaling and weighting steps, to combine responses to individual questions into an appropriately scaled score as a psychological measure with respect to the relevant individuals variables and the overall indices. The scaling and weighting functions employed will be dependent on the relative importance and reliability of the questions involved. Since the scaling and weighting functions are entirely dependent on the particular questionnaires used, they cannot be specified in general terms.

Figure 3:
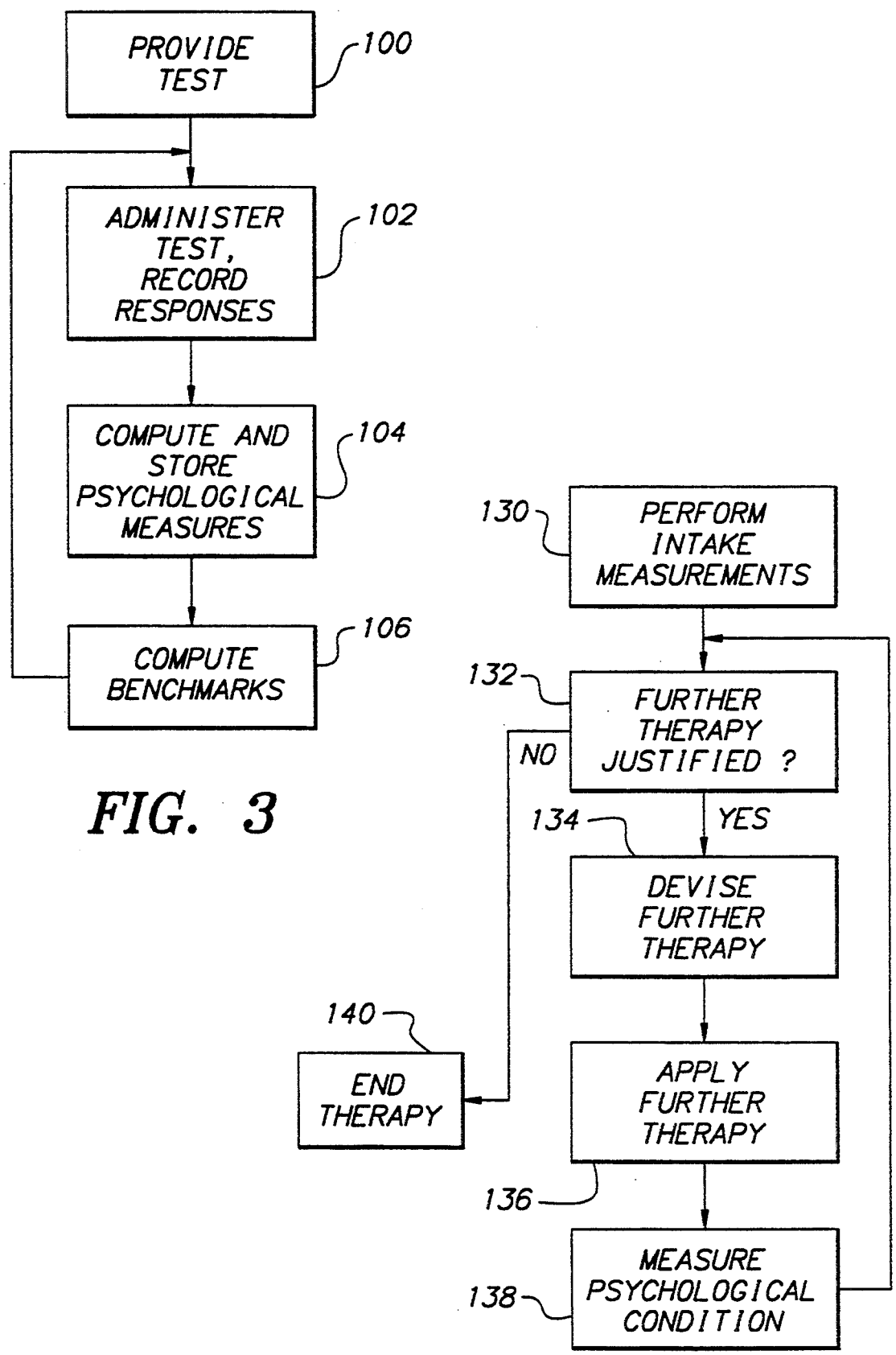
FIG. 3 is a flow diagram illustrating a method of establishing benchmark values for measured psychological variables.

With a suitable questionnaire and means for operating on the responses, it becomes possible to provide means for reliably measuring a person's psychological condition and changes therein. FIG. 3 is a flow chart illustrating a process which is of substantial value in such measurements. The process of FIG. 3 establishes objective benchmark values against which test results for individual patients may be compared. In step 100 a suitable test is provided, such as the test of Appendix A. The test is administered to a patient, preferably by obtaining both patient and clinician responses, and responses are recorded in step 102. In step 104, psychological measures are computed and stored based on the test results recorded in step 102. These psychological measures may be patient condition with respect to individual psychological variables and/or overall psychological indices, as previously described. In step 106, benchmarks are computed with respect to the computed psychological measures. Such benchmarks are values bearing a predetermined statistical relationship to the data set representing the psychological measures for groups of patient data in the database. Thus, the process is repeated by returning to step 102 and obtaining additional test results, preferably results for a large number of patients taken at different times during the course of their therapy. Thus, as the test is applied to increasing numbers of patients, the reliability of the benchmark values determined in step 106 increases. This provides objective and reliable self-validating benchmarks from which inferences regarding individual psychotherapy cases may be drawn.

For a given data set for a psychological measure, the benchmark may for example be established as a certain number of standard deviations with respect to the mean. The data distribution in such a data set will depend largely on the population from which the data is derived. Since a large data set is most easily obtained from a "mental health" population of persons seeking psychotherapy, a benchmark of normalcy for such a population may be established at a certain number of standard deviations above the mean. If comparative data is available regarding mental health populations and non-mental health populations, more accurate benchmarks might be obtained.

For the test of Appendix A, Applicant has determined a percentile measure of about 84 to be an appropriate benchmark of normalcy with respect to the mental health index, clinical assessment index, and the psychological variables which comprise them.

Figure 4:
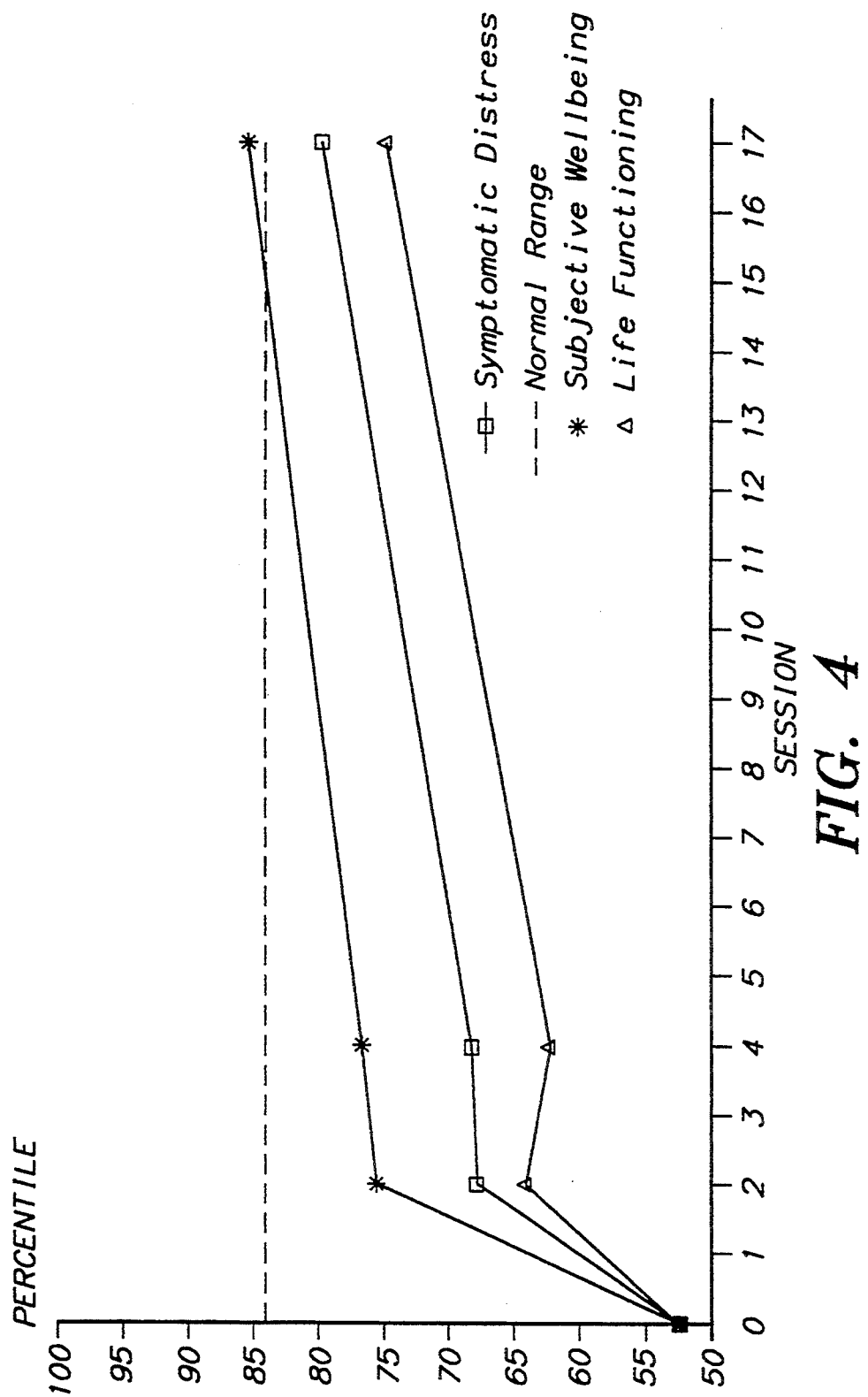
FIG. 4 is a dose-response graph for certain psychological variables.
Figure 5:
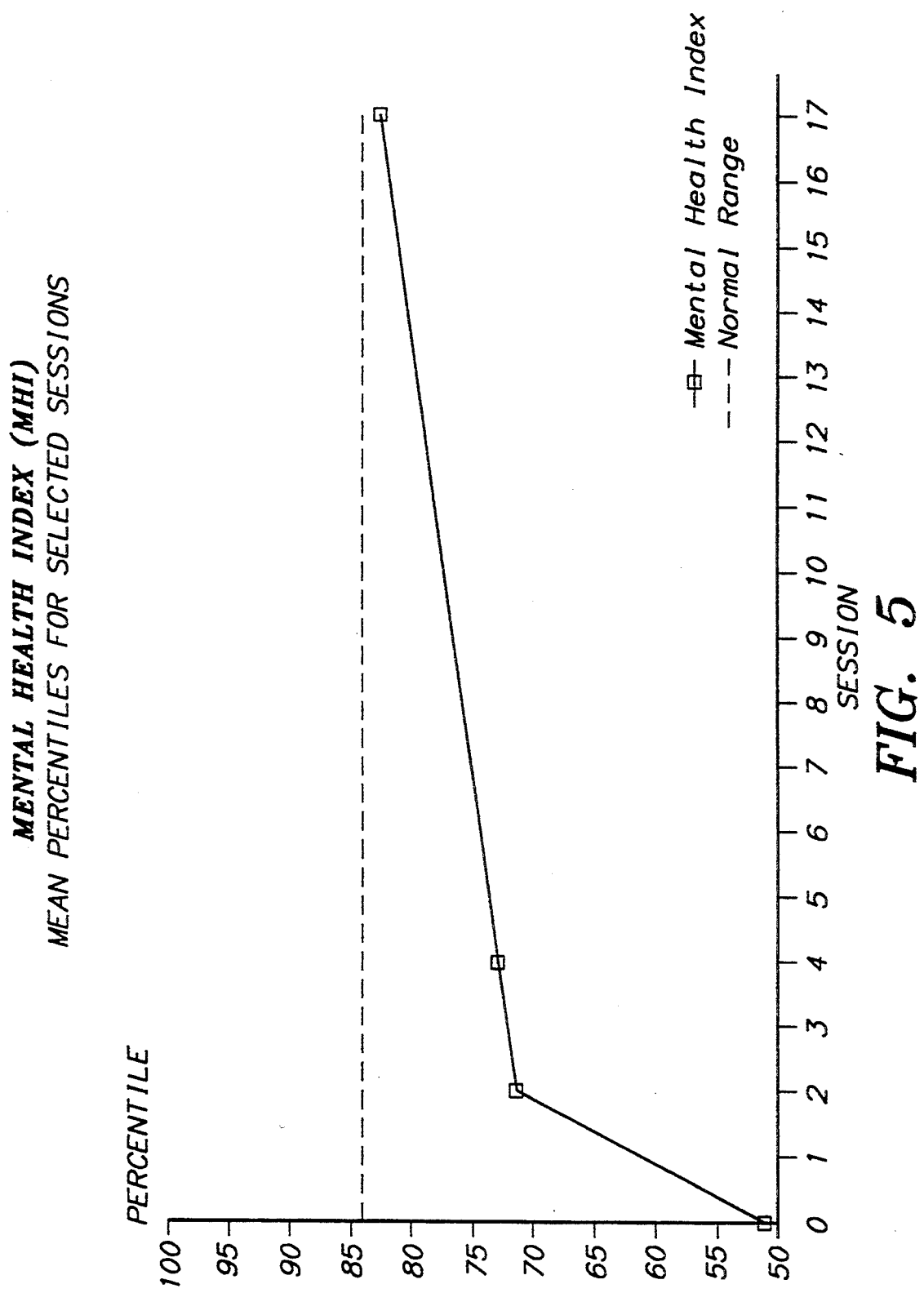
FIG. 5 is a dose-response graph for a composite mental health index computed from the measured variables of FIG. 4.

One particularly useful output format for data derived from a large database of patient test is a "dose-response" graph or chart of psychological measure versus psychotherapy dose, as illustrated in FIGS. 4 and 5. In each graph, the cumulative dose of psychotherapy is indicated on the X axis as the number of therapy sessions, and the mean percentiles for the psychological measures for data derived from the test of Appendix A is plotted on the Y axis. FIG. 4 shows the mean percentiles for the subjective well-being, symptomatic distress, and current life functioning psychological variables, and FIG. 4 shows the mean percentiles for mental health index, at intake and after 2, 4, and 17 psychotherapy sessions. Such charts provide data indicating varying benchmarks for expected improvement in psychological condition as a result of psychotherapy. The "normal" benchmark of about the 84th percentile is also shown. Psychological measures for a particular patient may be plotted on such a graph and compared with the benchmark curves.

Figure 6:
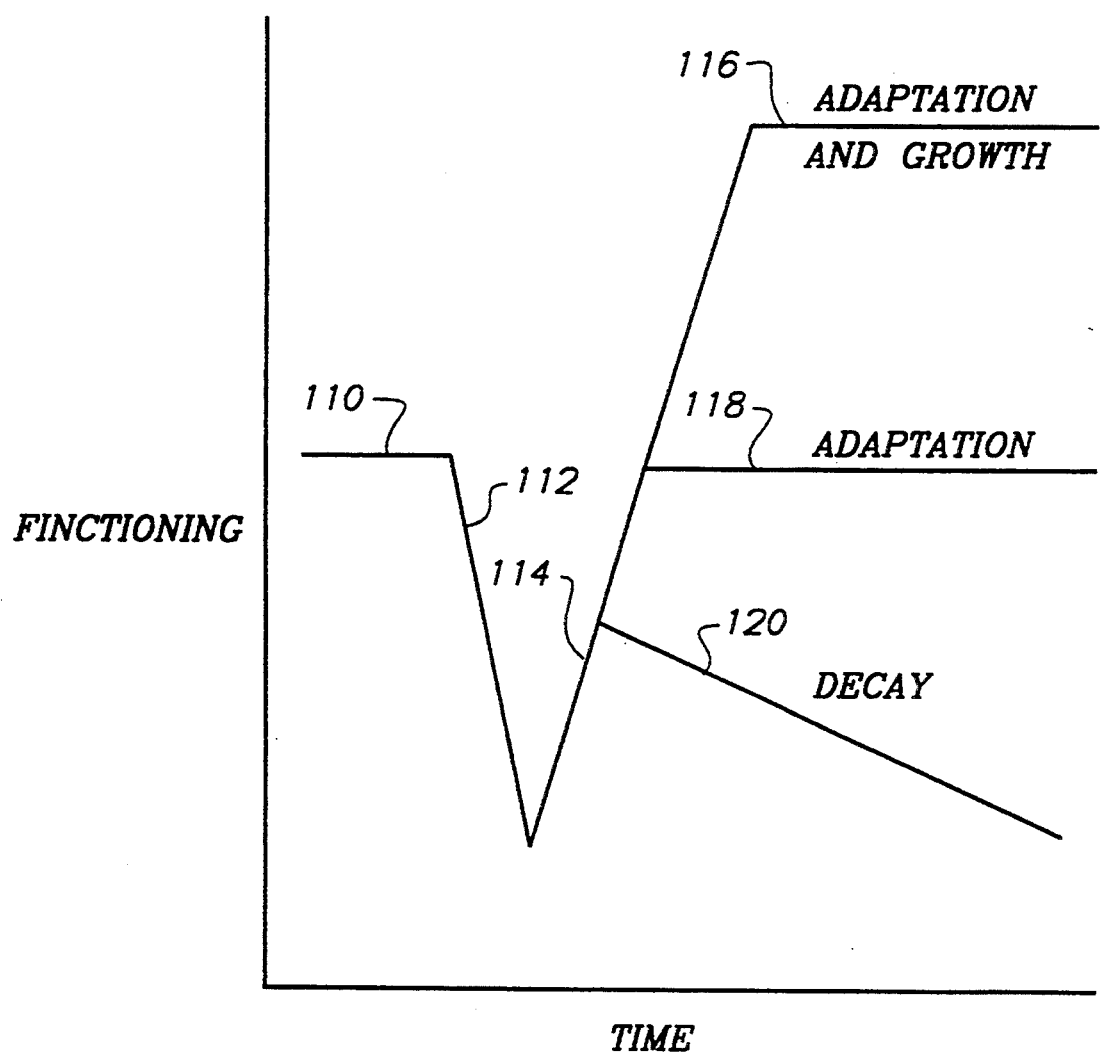
FIG. 6 is a graph illustrating typical courses a mental illness may take.

FIG. 6 is a diagram illustrating in a simplified fashion various typical courses of a mental illness, by graphing a measure of functioning determined by testing verses time (or dose of psychotherapy). After an initial period 110, a patient will often appear to show a worsening of condition during period 112 as the patient learns through therapy the nature and extent of the problem. This is typically followed by a period 114 of improvement as the therapy is effective in helping the patient to deal with the recognized problem, but after this improvement the illness may follow one of three courses. Course 116 represents adaption and growth, where the patient's condition improves and attains an acceptable level. Course 118 represents adaption without long-term improvement in condition. Course 120 represents decay, where the patient's condition worsens. By comparing the measurements taken at various times, preferably by graphing the measured data on such a chart, a therapy provider or case manager can objectively determine the course of the illness and effect of the therapy and use such information to control the therapy process.

Thus, FIG. 7 is a flow chart illustrating a method for feedback control of psychotherapy provided to a particular patient, which may be performed using the methods and apparatus previously described. In step 130, intake measurements are made for the patient such as by administering the questionnaire of Exhibit A, recording responses, and computing measures such as mental health and clinical assessment indices. In step 132, a determination is made based on the measurements as to whether therapy is justified. Initially this may indicate that the patient is sufficiently mentally healthy that therapy is not needed, and the process would terminate in step 140. If therapy is determined to be justified in step 132, a course of therapy is devised in step 134 and implemented in step 136. After a course of therapy, psychological condition is again measured in step 138, and the process returns to step 132 for a determination at that time of whether further therapy is justified. The process continues with devising and applying further therapy and testing to monitor condition and progress until a determination is made in step 132 that further treatment is not justified. In the early stages of therapy, such as in periods 110–114 at FIG. 6 further therapy will usually be justifiable. If course 116 is thereafter taken, a determination of when treatment has been appropriately completed can be made when the measurements of the patient's condition equal or exceed the benchmark "normal" value, and therapy may be terminated. If courses 118 or 120 are followed by the patient, the failure to progress may be detected at an early stage and appropriate action taken. Such action may include a change of focus of therapy and/or change of therapist in steps 134 and 136. If such actions are successful, the patient will progress toward benchmark "normalcy" and may eventually be determined as a therapeutic success. If the failure-to-progress courses 118 and 120 persist, and reasonable efforts to provide appropriate therapy have been made, then at a certain point in time therapy may be terminated because it is unlikely to be successful and further therapy is therefore unjustifiable. Using this method, the treatment decisions made by a therapist, case manager, or party paying for the therapy can be objectively documented and explained.

Figure 8:
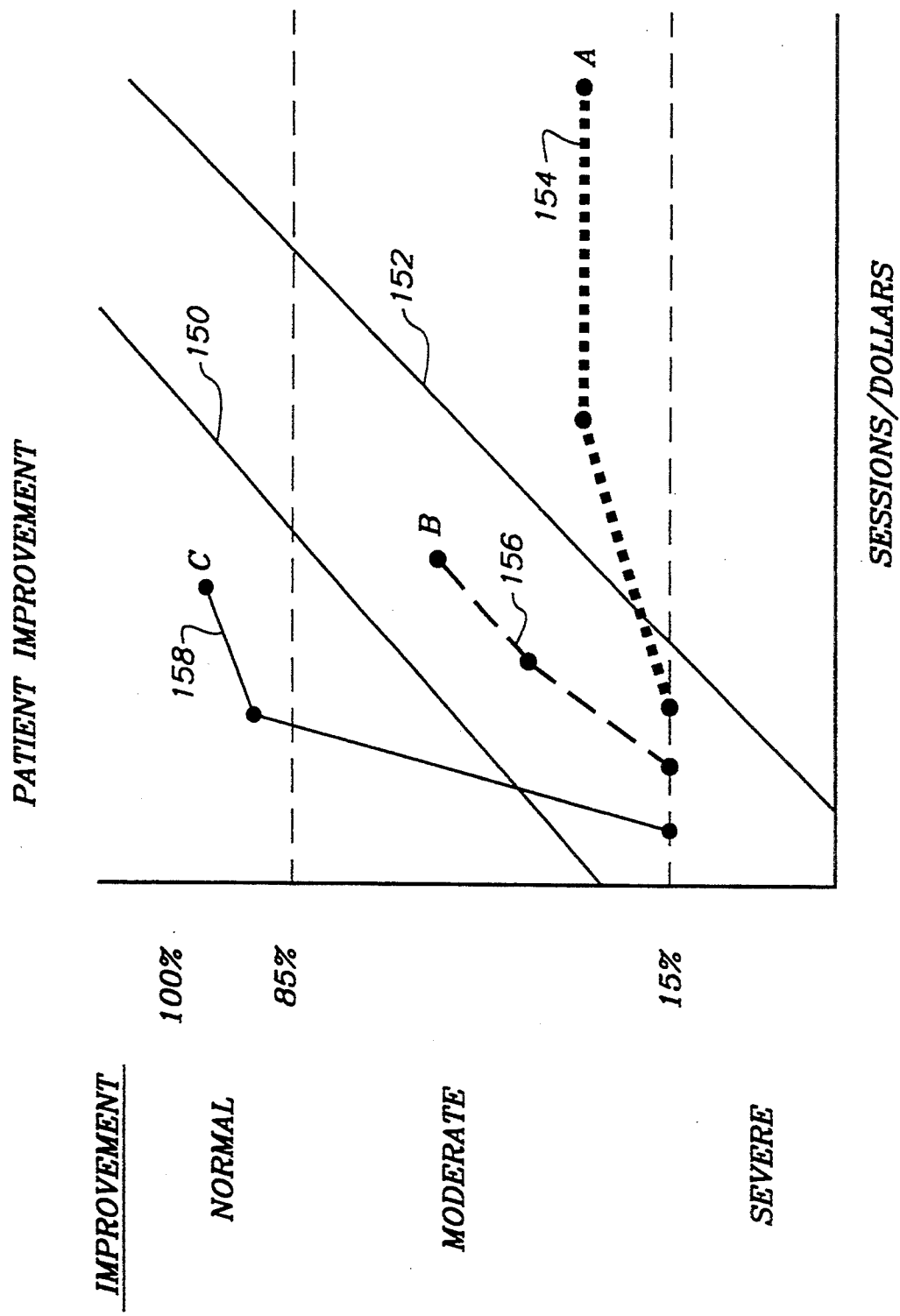
FIG. 8 is another dose-response graph.

FIG. 8 is a dose-response diagram providing an easily-visualized presentation of a patient's condition and progress. A psychological measure, such as the mental health index, is computed for a patient based on tests taken at various times and plotted against psychotherapy dose, which as indicated may be the number of therapy sessions or their monetary cost. In addition to the 84th percentile benchmark for a normalcy of condition, a pair of benchmark curves 150 and 152 are plotted which represent the bounds of normal improvement in condition versus dose. FIG. 4 illustrates a mean dose-response curve computed from the data in the database; the upper and lower bounds 150 and 152 may be computed from the same data as a certain number of standard deviations above and below the mean, respectively.

Curves 154, 156, and 158 illustrate plots of psychological measures computed for patients A, B, and C, respectively. In the method of FIG. 7, measurements in step 138 of patient B indicate that therapy is progressing as expected. Therefore, in step 132 it would be determined that further therapy is justified, and a case manager might authorize a specific number of further sessions. The course of therapy is appropriate, and in step 134 the further therapy devised would be a continuation of the previously-successful method. Measurements of patient C in step 138 indicate that therapy is progressing better than expected; only a limited amount of further therapy would be determined to be justified in step 134, and treatment may be terminated early. Measurements of patient A in step 138 indicate that the patient's condition is improving more slowly than expected. The measurements provide a flag to the therapist and the case manager indicating that a change in the therapy method might be appropriately made in step 134 and that while further therapy may be justified, the patient's condition should be monitored closely so that treatment can be terminated if further changes in condition show that treatment is unlikely to be successful in achieving normal psychological measures.

The following is an example of testing results obtained over a course of the psychotherapy of a particular patient using the methods and apparatus of the invention.

Patient 30075—98+ Session Treatment

Presentation

Patient is a young, white, single, woman. She completed college and is currently working at part time jobs.

"I have been disappointed in my working/job situation. I feel as if I have been misused and used by my employer in this present job as well as in my previous job. I have lost my drive for achievement and challenge. With my boredom for work, my social life doesn't seem to be as exciting as it should be. So I feel bored at work as well as being bored with my social life. I think I am confused as to whether it's my personality that is expecting too much from life or that I am not receiving the full amount of happiness that I should. I want a great deal from life and I feel I am falling short, so I guess I need to realize now to deal with the present boredom I have with my job and social life."

Seven years ago she had some family therapy and six years ago she had six months of individual psychotherapy.

The intake diagnosis was: Dysthymia.

Figure 9:
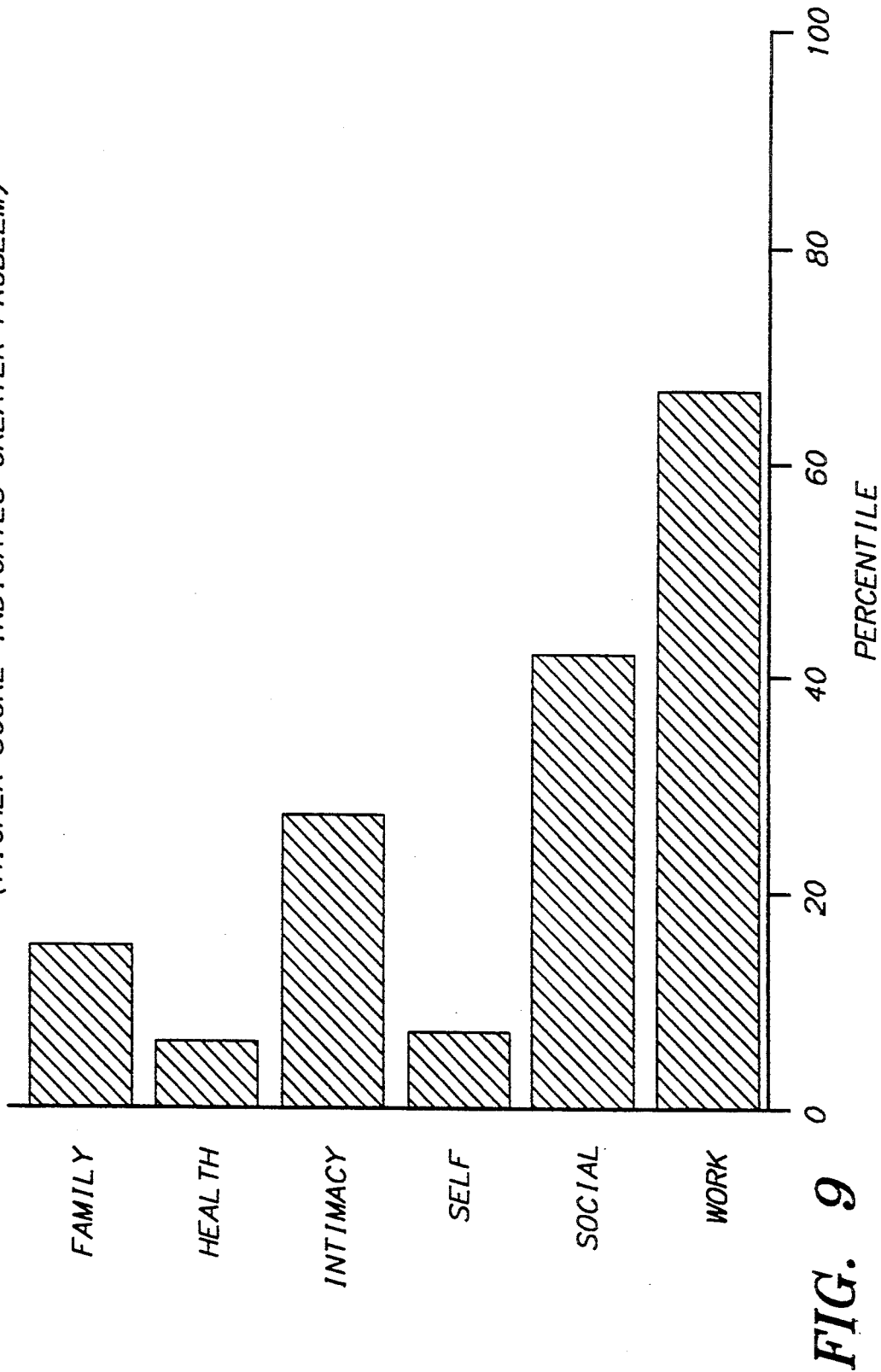
FIG. 9 is a bar graph of patient presenting problems measured in an example.
Figure 10:
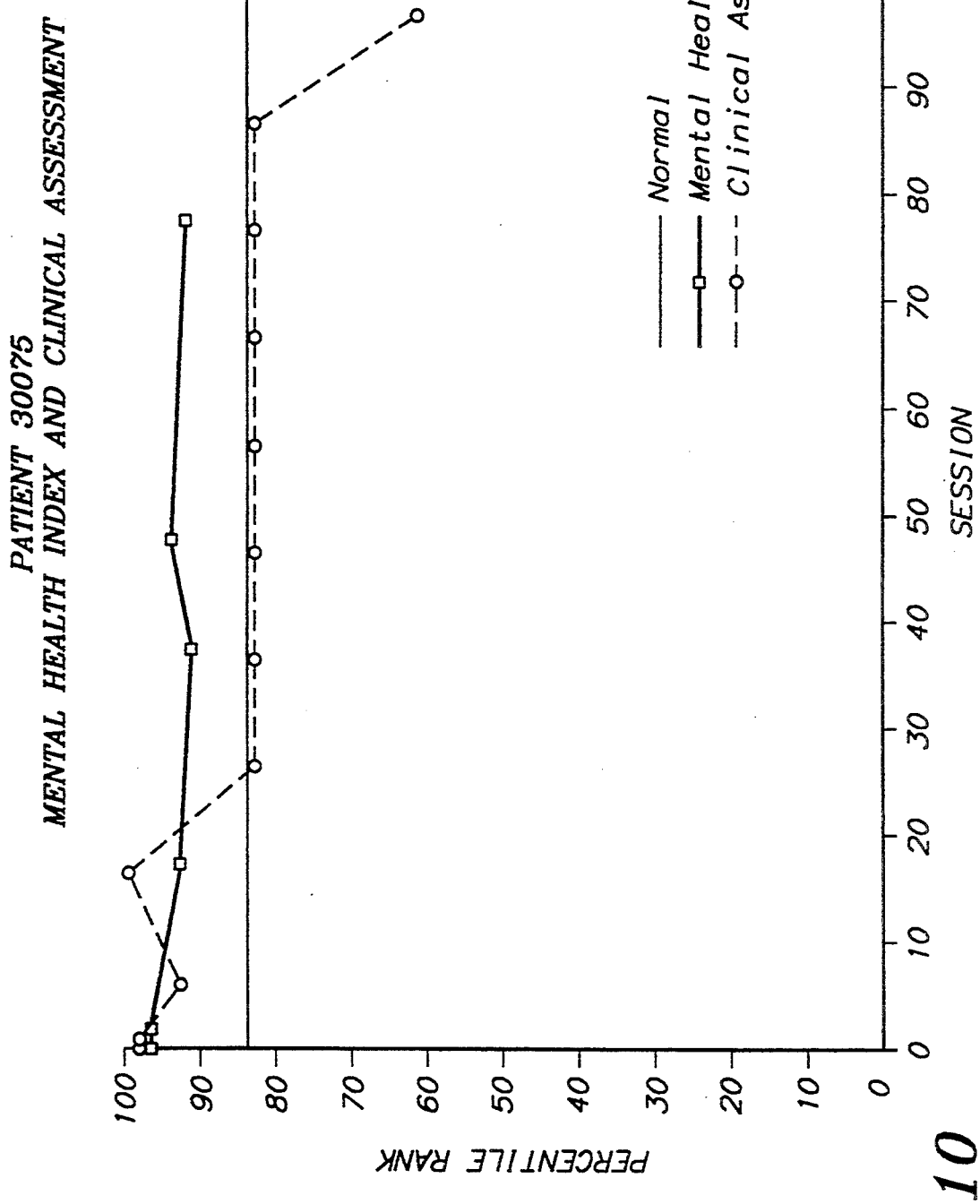
FIG. 10 is a dose-response graph for the patient of the example.

FIG. 9 is a bar graph showing the percentile scores of the patient of the example with respect to presenting problems. FIG. 10 is a dose-response curve illustrating mental health index and clinical assessment index for the patient based on tests administered at various times over a 98 session course of psychotherapy. FIG. 11 is a listing of the patient's percentile rank with respect to the subjective well-being, symptomatic distress, and current life functioning variables of the composite mental health index, measured at intake and at session 77 of therapy. Such figures may be produced as outputs of a system in accordance with the invention.

These figures, and particularly FIG. 10, show that the patient did not need psychotherapy, and that the course of therapy resulted if anything in a worsening of the patient's condition. The 98 sessions devoted to this patient represent scarce and expensive resources which would have been better devoted to other patients who might benefit from them. In addition to permitting feedback control over the therapy administered to an individual patient, the system of the invention permits rational allocation of therapy resources among various patients and financial resources supporting the therapy among various individual therapists, therapy organizations, or other therapy providers.

Figure 12:
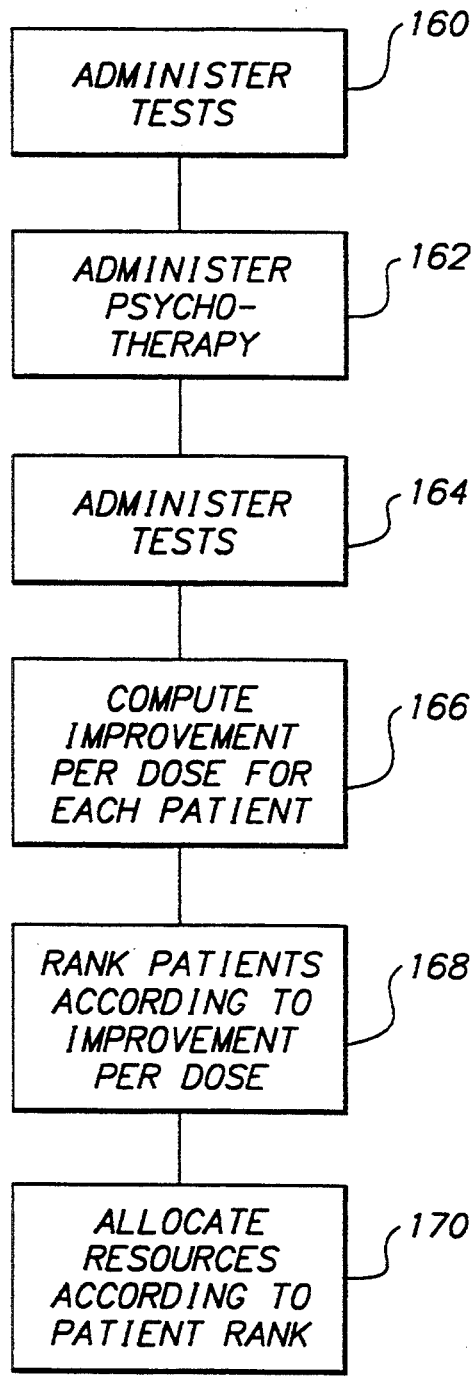
FIG. 12 is a flow diagram of a method of allocating psychotherapy resources among patients.

FIG. 12 is a flow diagram of a method of allocating psychotherapy resources among a group of patients. In steps 160–164, psychological tests are administered to the patients in the group before and after a course of psychotherapy. These steps will in general take place at different times for different patients, and may be repeated as previously described. Data from such tests is desirably stored in a database, as previously described. In step 166, improvement per dose is computed for each patient in the group. The patients are ranked in order in accordance with their computed improvement per dose in step 168, and psychotherapy resources are allocated among the patients in the group according to their ranking in step 170. Resources may be so allocated in a large number of different ways. For example, for the patient group consisting of patients A, B, and C of FIG. 8, resources might be allocated preferentially to C, then B, then A. Therapy might be terminated for patients whose improvement per dose has remained below a benchmark value for a certain length of time. Algorithms for allocating resources among a patient group may be stored in database 40 of FIG. 1.

Figure 13:
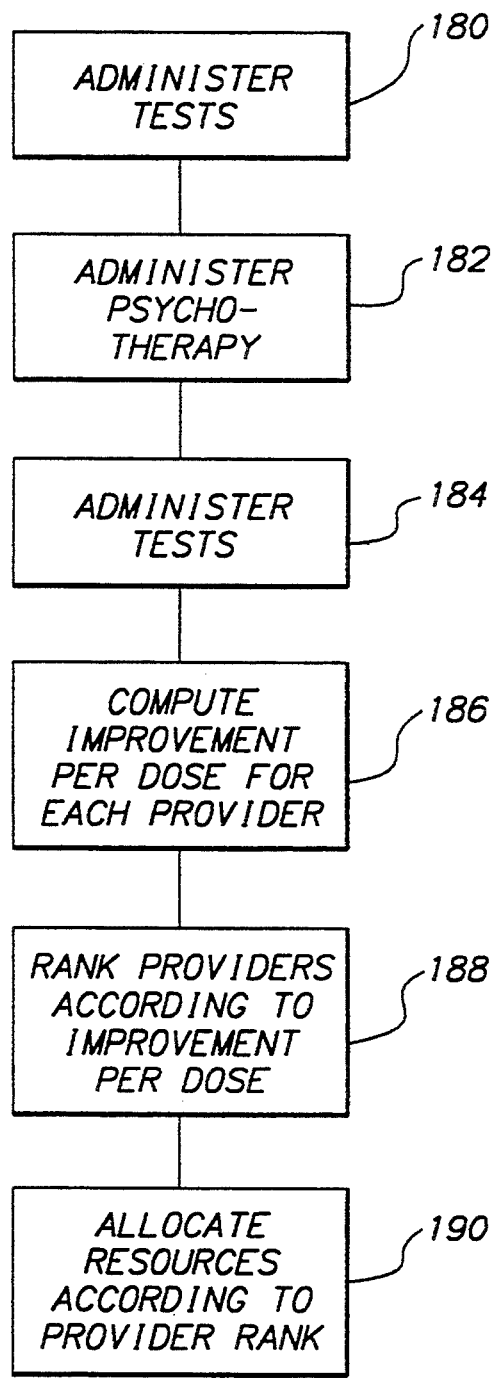
FIG. 13 is a flow diagram of a method of allocating psychotherapy resources among providers.

FIG. 13 is a flow diagram of a method of allocating resources supporting therapy among various providers. In steps 180–184, the test-therapy-test sequence is again utilized. When sufficient data has been obtained for the providers administering the therapy, in step 186 the improvement per dose is computed for each provider in the group based on the test results of the patients being treated by the provider. In step 188, the providers are ranked in order according to their computed improvement per dose, and resources are allocated in step 190 according to the ranking. Thus, a therapist group can evaluate the relative effectiveness of its members and take such steps as discharging therapists whose improvement-per-dose measure is below a benchmark or distribute cases among the members in accordance with their capabilities. A company or insurer can authorize treatment only by therapists having an improvement per dose above a benchmark. A variety of other resource allocation methods may be employed based upon such data.

While the apparatus shown in FIG. 1 may be configured as a stand-alone system, it is believed that the invention may have greatest utility when the elements in the apparatus are distributed in a network. For instance, a hub-and-spoke network may be established in which a large number of nodes, each of which may represent a therapy provider, uses apparatus as shown in FIG. 1. Each node communicates data to the hub for all tests administered at the node, and the hub maintains a large database comprising patient records from all of the nodes. The large hub database permits more accurate benchmarks to be computed, and the benchmarks computed at the hub may be communicated to each node. In this way, each node can input its own data and compute its own psychological measures without the necessity of obtaining large amounts of data and maintaining it resident at the node.

It will be understood that the foregoing is merely illustrative of the principles of this invention and that various modifications can be made by those skilled in the art without departing from the scope and spirit of the invention.

What is claimed is:

1. An apparatus for measuring the psychological condition of a patient comprising:

means for receiving psychological test data relating to at least one patient and for presenting the received data as digital signals, said test data including data obtained with respect to a patient at various times during a time interval, said test data including data relating to at least one psychological variable;

means for examining said digital signals and selecting therefrom the signal portions relating to said at least one psychological variable;

means for computing a single-valued quantity for each of said various times, representing the psychological condition of a patient with respect to said at least one psychological variable, from said selected digital signals; and means for comparing said single-valued quantity computed for each of said various times with a predetermined benchmark quantity representing a benchmark psychological condition to obtain an indication of the patient's psychological condition with respect to said benchmark condition and an indication of the change in the patient's psychological condition over the time interval;

wherein said comparing means includes means for comparing time changes in said single-valued quantity with a predetermined benchmark quantity representing a time rate of change of psychological condition, to obtain an indication of the time rate of change in the patient's psychological condition with respect to said benchmark rate.

2. An apparatus for measuring the psychological condition of a patient comprising:

means for receiving psychological test data relating to at least one patient and for presenting the received data as digital signals, said test data including data relating to at least one psychological variable, said test data including data obtained at various times with respect to each of a plurality of patients;

means for examining said digital signals and selecting therefrom the signal portions relating to said at least one psychological variable;

means for computing a single-valued quantity, representing the psychological condition of a patient with respect to said at least one psychological variable, from said selected digital signals, said means for computing including means for computing a predetermined benchmark quantity representing a benchmark psychological condition from said digital signals; and means for comparing said single-valued quantity with said predetermined benchmark quantity to obtain an indication of the patient's psychological condition with respect to said benchmark condition;

wherein said predetermined benchmark quantity represents a time rate of change of psychological condition.

* * * * *

UNITED STATES PATENT AND TRADEMARK OFFICE
CERTIFICATE OF CORRECTION

PATENT NO. : 5,435,324
DATED : Jul. 25, 1995
INVENTOR(S) : Peter L. Brill

It is certified that error appears in the above-indentified patent and that said Letters Patent is hereby corrected as shown below:

Immediately after the claims at column 12, line 47, insert Appendix A and Appendix B attached hereto.

Signed and Sealed this

Tenth Day of October, 1995

Attest:

BRUCE LEHMAN

Attesting Officer

Commissioner of Patents and Trademarks

APPENDIX "A"

OUTPATIENT THERAPY EFFECTIVENESS TRACKING SYSTEM

Kenneth I. Howard, Ph.D.
Northwestern University

Peter L. Brill, M.D.
Integra®, Inc.

Robert J. Lueger, Ph.D.
Marquette University

Michael T. O'Mahoney, Ph.D.
Mercy Center for Health Care Services

PERSONAL INFORMATION

DO NOT COMPLETE THIS SECTION IF YOU HAVE COMPLETED IT BEFORE.

<u>Age</u>

① Less than 18 years old
② 18 - 24 years old
③ 25 - 34 years old
④ 35 - 44 years old
⑤ 45 - 54 years old
⑥ 55 - 64 years old
⑦ 65 years or older <u>Gender</u>

① Male
② Female

<u>Ethnicity</u>

① White
② African-American
③ Oriental
④ Hispanic
⑤ Native American
⑥ Other

1. Are you currently employed?

① No
   ② Employed part-time
   ③ Employed full-time

2. Are you currently a student in school or in a training program?

① No
   ② Studying part-time
   ③ Studying full-time

3. How much education have you completed?

① Grammar school or less
   ② Some high school
   ③ High School
   ④ Some college
   ⑤ College graduate
   ⑥ Some professional/ graduate school
   ⑦ Completed professional/ graduate school 4. What is your present marital status?

① Single (never married)
   ② Married (first)
   ③ Remarried
   ④ Separated
   ⑤ Divorced
   ⑥ Widowed © Copyright. Integra©, Inc. 1992. All Rights Reserved.

PERSONAL INFORMATION
(continued)

> DO NOT COMPLETE THIS SECTION IF YOU HAVE COMPLETED IT BEFORE.

5. How many children do you have (Circle One)?

0     1     2     3     4     5     6     7     More than 7

6. With whom do you live? (Check all that apply.)

| | | | |
    |---|---|---|---|
    | ① | Live alone | ⑤ | Live with romantic partner |
    | ② | Live with roommate(s) | ⑥ | Live with parent(s) |
    | ③ | Live with spouse | ⑦ | Live with other relative |
    | ④ | Live with child(ren) | ⑧ | Other |

© Copyright. Integra©, Inc. 1992. All Rights Reserved.

TREATMENT NEED AND EXPECTATIONS

DO NOT COMPLETE THIS SECTION IF YOU HAVE COMPLETED IT BEFORE.

1. How much counseling or psychotherapy have you had in the past?

① None
   ② Less than one month
   ③ One to three months
   ④ Three to seven months
   ⑤ More than seven months 2. How important to you is it to enter counseling or psychotherapy at this time?

① It is absolutely essential to me.
   ② It is very important to me.
   ③ It is moderately important to me.
   ④ It is somewhat important to me.
   ⑤ It is not important to me at all.

3. How difficult is it going to be for you to be in counseling/ psychotherapy (in terms of effort, cost, lost job time, transportation, other people's opinions, etc.)?

① It will be easy for me.
   ② It will be a little difficult.
   ③ It will be pretty difficult.
   ④ It will be very difficult.
   ⑤ It will be extremely difficult.
   ⑥ It will be impossible.

4. How confident are you that counseling or psychotherapy will be successful in helping you with your problem(s)?

① Not at all confident.
   ② Slightly confident.
   ③ Pretty confident.
   ④ Very confident.

5. What is your best guess as to how long counseling or psychotherapy will last?

① 1-3 weeks
   ② 4-8 weeks
   ③ 2-6 months
   ④ 6-12 months
   ⑤ 1-2 years
   ⑥ 2-5 years
   ⑦ More than 5 years © Copyright. Integra©, Inc. 1992. All Rights Reserved.

TREATMENT NEED AND EXPECTATIONS
(Continued)

DO NOT COMPLETE THIS SECTION IF YOU HAVE COMPLETED IT BEFORE.

6. When you finish counseling or psychotherapy, how well do you feel that you will be getting along emotionally and psychologically?

I WILL BE GETTING ALONG:

① Quite poorly; I will be barely able to manage to deal with things.
   ② Fairly poorly; life was pretty tough for me at times.
   ③ So-so; I will be able to manage to keep going with some effort.
   ④ Fairly well; I will have my ups and downs.
   ⑤ Quite well; I will have no important complaints.
   ⑥ Very well; much the way I would like to.

7. Please think back to when you decided to call for an appointment. At that time, how well did you feel that you were getting along emotionally and psychologically?

I WAS GETTING ALONG:

① Quite poorly; I will be barely able to manage to deal with things.
   ② Fairly poorly; life was pretty tough for me at times.
   ③ So-so; I will be able to manage to keep going with some effort
   ④ Fairly well; I will have my ups and downs.
   ⑤ Quite well; I will have no important complaints.
   ⑥ Very well; much the way I would like to.

8. When you decided to call for an appointment, how upset or distressed had you been feeling?

I HAD BEEN FEELING:

① Extremely distressed         ④ Slightly distressed
   ② Very distressed              ⑤ Not at all distressed
   ③ Pretty distressed © Copyright. Integra©, Inc. 1992. All Rights Reserved.

PRESENTING PROBLEMS

BEST AVAILABLE COPY

DO NOT COMPLETE THIS SECTION IF YOU HAVE COMPLETED IT BEFORE

Please rate the extent to which each of these problems is a reason for your seeking psychotherapy now by filling in the circle of the appropriate response for each problem.

I AM SEEKING PSYCHOTHERAPY BECAUSE OF:

| | | Not At All | | Some | | Very Much |
|---|---|---|---|---|---|---|
| 1. | Problems with my spouse or romantic partner. | ① | ② | ③ | ④ | ⑤ |
| 2. | Difficulty forming or maintaining an intimate relationship. | ① | ② | ③ | ④ | ⑤ |
| 3. | A sexual problem. | ① | ② | ③ | ④ | ⑤ |
| 4. | Problems getting along with a friend or friends. | ① | ② | ③ | ④ | ⑤ |
| 5. | An unsatisfactory social life. | ① | ② | ③ | ④ | ⑤ |
| 6. | Difficulties getting along with family members (not spouse). | ① | ② | ③ | ④ | ⑤ |
| 7. | Problems getting along with people in general. | ① | ② | ③ | ④ | ⑤ |
| 8. | Feeling uncomfortable with people in general. | ① | ② | ③ | ④ | ⑤ |
| 9. | Not getting things done at work or school. | ① | ② | ③ | ④ | ⑤ |
| 10. | Problems handling family responsibilities. | ① | ② | ③ | ④ | ⑤ |
| 11. | Not having a sense of direction or goals in life. | ① | ② | ③ | ④ | ⑤ |
| 12. | Not managing life well in general. | ① | ② | ③ | ④ | ⑤ |
| 13. | Low self-esteem. | ① | ② | ③ | ④ | ⑤ |
| 14. | Not understanding myself. | ① | ② | ③ | ④ | ⑤ |
| 15. | Reacting too emotionally to events. | ① | ② | ③ | ④ | ⑤ |
| 16. | Feeling distress, anxiety, depression, or anger. | ① | ② | ③ | ④ | ⑤ |
| 17. | A physical problem, such as illness, pain or medical symptoms. | ① | ② | ③ | ④ | ⑤ |
| 18. | Alcohol or drug use. | ① | ② | ③ | ④ | ⑤ |
| 19. | An eating problem. | ① | ② | ③ | ④ | ⑤ |
| 20. | Problems developing or managing my career. | ① | ② | ③ | ④ | ⑤ |
| 21. | Missing work or school or not getting there on time. | ① | ② | ③ | ④ | ⑤ |
| 22. | Difficulties caused by the substance abuse or emotional problems of a member of my family. | ① | ② | ③ | ④ | ⑤ |
| 23. | Another problem _____ | ① | ② | ③ | ④ | ⑤ |

© Copyright. Integra©, Inc. 1992. All Rights Reserved.

THERAPIST RATINGS

1. How well does your therapist seem to understand what you are feeling and thinking?

① Understands exactly how I think and feel.

② Understands very well how I think and feel.

③ Understands pretty well, but there are some things he/she doesn't seem to grasp.

④ Doesn't understand too well how I think and feel.

2. How helpful do you feel your therapist is?

① Completely helpful.      ④ Somewhat helpful.

② Very helpful.            ⑤ Slightly helpful.

③ Pretty helpful.          ⑥ Not at all helpful.

MY THERAPIST:

|   |   | Not at All | Some | Pretty Much | Very Much |
|---|---|---|---|---|---|
| 1. | Is attentive to what I try to get across. | ○ | ① | ② | ③ |
| 2. | Is friendly and warm towards me. | ○ | ① | ② | ③ |
| 3. | Seems cheerful. | ○ | ① | ② | ③ |
| 4. | Seems involved. | ○ | ① | ② | ③ |
| 5. | Seems confident. | ○ | ① | ② | ③ |
| 6. | Seems interested. | ○ | ① | ② | ③ |
| 7. | Seems optimistic. | ○ | ① | ② | ③ |

© Copyright. Integra©, Inc. 1992. All Rights Reserved.

CURRENT WELL-BEING

1. At the present time, how upset or distressed have you been feeling?

① Not at all distressed.
   ② Slightly distressed.
   ③ Pretty distressed.
   ④ Very distressed.
   ⑤ Extremely distressed.

2. At the present time, how energetic and healthy have you been feeling?

① Not at all energetic and healthy.
   ② Slightly energetic and healthy.
   ③ Pretty energetic and healthy.
   ④ Very energetic and healthy.
   ⑤ Extremely energetic and healthy.

3. At the present time, how well do you feel that you are getting along emotionally and psychologically?

① Quite poorly; I can barely manage to deal with things.
   ② Fairly poorly; life is pretty tough for me at times.
   ③ So-so; I manage to keep going with some effort.
   ④ Fairly well; I have my ups and downs.
   ⑤ Quite well; I have no important complaints.
   ⑥ Very well; much the way I would like to.

4. At the present time, how much do you feel you have benefitted from this counseling or psychotherapy? *(Not Applicable if this is your first session with this therapist.)*

I WOULD RATE MYSELF AS:

○ Not Applicable
   ① Considerably improved.
   ② Moderately improved.
   ③ Slightly improved.
   ④ Unchanged.
   ⑤ Slightly worse.
   ⑥ Moderately worse.
   ⑦ Considerably worse.

© Copyright. Integra©, Inc. 1992. All Rights Reserved.

AT THE PRESENT TIME, HOW SATISFIED ARE YOU WITH:

|   |   | Not Applicable | | Not at all Satisfied | | Pretty Satisfied | | Extremely Satisfied |
|---|---|---|---|---|---|---|---|---|
| 1. | The way you are managing your life (meeting personal goals, self-esteem, self-control)? | ○ | ① | ② | ③ | ④ | ⑤ |
| 2. | Your job, progress in school, performance of household activities? | ○ | ① | ② | ③ | ④ | ⑤ |
| 3. | Your intimate relationships (spouse, romantic partner)? | ○ | ① | ② | ③ | ④ | ⑤ |
| 4. | Your social relationships (friends, other than your relatives)? | ○ | ① | ② | ③ | ④ | ⑤ |
| 5. | Your family relationships (parents, children, other relatives)? | ○ | ① | ② | ③ | ④ | ⑤ |
| 6. | Your health habits (exercise, eating habits)? | ○ | ① | ② | ③ | ④ | ⑤ |
| 7. | Your life in general? | ○ | ① | ② | ③ | ④ | ⑤ |

© Copyright. Integra©, Inc. 1992. All Rights Reserved.

CURRENT LIFE FUNCTIONING

Below are some ways in which people's emotional or psychological problems interfere with their functioning. Please read each item carefully and fill in the circle which corresponds to the response that best describes your present situation. Please use the following rating system:

- ○ = Not applicable
- ① = Not at all
- ② = A little bit
- ③ = Moderately
- ④ = Quite a bit
- ⑤ = Extremely

MY EMOTIONAL/PSYCHOLOGICAL PROBLEMS INTERFERE WITH MY:

| | | Not applicable | Not at all | | Moderately | | Extremely |
|---|---|---|---|---|---|---|---|
| 1. | Ability to perform routine tasks. | ○ | ① | ② | ③ | ④ | ⑤ |
| 2. | Interactions with friends. | ○ | ① | ② | ③ | ④ | ⑤ |
| 3. | Interactions with people at work. | ○ | ① | ② | ③ | ④ | ⑤ |
| 4. | Interactions with my spouse/romantic partner. | ○ | ① | ② | ③ | ④ | ⑤ |
| 5. | Ability to maintain my personal appearance. | ○ | ① | ② | ③ | ④ | ⑤ |
| 6. | Interaction with my parents. | ○ | ① | ② | ③ | ④ | ⑤ |
| 7. | Interaction with my siblings. | ○ | ① | ② | ③ | ④ | ⑤ |
| 8. | Ability to concentrate and complete tasks. | ○ | ① | ② | ③ | ④ | ⑤ |
| 9. | Performance at work or school. | ○ | ① | ② | ③ | ④ | ⑤ |
| 10. | Carrying out family responsibilities. | ○ | ① | ② | ③ | ④ | ⑤ |
| 11. | Participation in physical activities. | ○ | ① | ② | ③ | ④ | ⑤ |
| 12. | Participation in social activities. | ○ | ① | ② | ③ | ④ | ⑤ |
| 13. | Ability to function as an independent person. | ○ | ① | ② | ③ | ④ | ⑤ |
| 14. | Developing or managing my career. | ○ | ① | ② | ③ | ④ | ⑤ |
| 15. | Ability to manage my finances. | ○ | ① | ② | ③ | ④ | ⑤ |
| 16. | Planning and enjoying leisure time activities. | ○ | ① | ② | ③ | ④ | ⑤ |
| 17. | Being the kind of person I would like to be. | ○ | ① | ② | ③ | ④ | ⑤ |
| 18. | Ability to form or sustain intimate relationships. | ○ | ① | ② | ③ | ④ | ⑤ |
| 19. | Enjoyment of sexual activities. | ○ | ① | ② | ③ | ④ | ⑤ |
| 20. | Maintaining good health habits. | ○ | ① | ② | ③ | ④ | ⑤ |

© Copyright. Integra©, Inc. 1992. All Rights Reserved.

CURRENT LIFE FUNCTIONING
(Continued)

|     |                                                      | Not applicable | Not at all | | Moderately | | Extremely |
|-----|------------------------------------------------------|:--------------:|:----------:|:-:|:--------:|:-:|:---------:|
| 21. | Creative activities.                                 | ○ | ① | ② | ③ | ④ | ⑤ |
| 22. | Ability to control myself and stay out of trouble.   | ○ | ① | ② | ③ | ④ | ⑤ |
| 23. | Attending work or school or getting there on time.   | ○ | ① | ② | ③ | ④ | ⑤ |
| 24. | Ability to be comfortable with people.               | ○ | ① | ② | ③ | ④ | ⑤ |

© Copyright. Integra©, Inc. 1992. All Rights Reserved.

CURRENT SYMPTOMS

Below is a list of problems and complaints that people sometimes have. Read each item carefully and fill in the circle which corresponds to the response that best describes HOW OFTEN YOU HAVE HAD EACH EXPERIENCE IN THE PAST MONTH. Please use the following rating system:

- ○    Not At All
- ①    Once or Twice
- ②    Several Times
- ③    Often
- ④    Most of the Time
- ⑤    All of the Time

|   |   | Not at All | Once or Twice | | Often | | All of the Time |
|---|---|---|---|---|---|---|---|
| 1. | Having repetitive thoughts that I cannot get rid of. | ○ | ① | ② | ③ | ④ | ⑤ |
| 2. | Problems at work or school because of my alcohol or drug use. | ○ | ① | ② | ③ | ④ | ⑤ |
| 3. | Thoughts that seemed to race through my mind. | ○ | ① | ② | ③ | ④ | ⑤ |
| 4. | Avoiding places that seemed too closed in. | ○ | ① | ② | ③ | ④ | ⑤ |
| 5. | Headaches. | ○ | ① | ② | ③ | ④ | ⑤ |
| 6. | Feeling sad most of the day. | ○ | ① | ② | ③ | ④ | ⑤ |
| 7. | Trying to push thoughts out of my mind. | ○ | ① | ② | ③ | ④ | ⑤ |
| 8. | Guilt or remorse over my alcohol or drug use. | ○ | ① | ② | ③ | ④ | ⑤ |
| 9. | Being sluggish or lethargic. | ○ | ① | ② | ③ | ④ | ⑤ |
| 10. | Thoughts about ending my life. | ○ | ① | ② | ③ | ④ | ⑤ |
| 11. | Muscular tension or aches. | ○ | ① | ② | ③ | ④ | ⑤ |
| 12. | Feeling blocked at work or school. | ○ | ① | ② | ③ | ④ | ⑤ |
| 13. | Difficulty concentrating. | ○ | ① | ② | ③ | ④ | ⑤ |
| 14. | Feeling hopeless about the future. | ○ | ① | ② | ③ | ④ | ⑤ |
| 15. | Being irritable and easily angered. | ○ | ① | ② | ③ | ④ | ⑤ |
| 16. | Afraid of leaving my home. | ○ | ① | ② | ③ | ④ | ⑤ |
| 17. | Engaging in repetitive behaviors to calm myself. | ○ | ① | ② | ③ | ④ | ⑤ |
| 18. | Dizziness. | ○ | ① | ② | ③ | ④ | ⑤ |
| 19. | Feeling ill or rundown. | ○ | ① | ② | ③ | ④ | ⑤ |
| 20. | Trouble falling asleep. | ○ | ① | ② | ③ | ④ | ⑤ |

© Copyright. Integra©, Inc. 1992. All Rights Reserved.

Read each item carefully and fill in the circle which corresponds to the response that best describes HOW OFTEN YOU HAVE HAD EACH EXPERIENCE IN THE PAST MONTH. Please use the following rating system:

|   |   |
|---|---|
| ⓪ | Not At All |
| ① | Once or Twice |
| ② | Several Times |
| ③ | Often |
| ④ | Most of the Time |
| ⑤ | All of the Time |

|   |   | Not at All | Once or Twice | | Often | | All of the Time |
|---|---|---|---|---|---|---|---|
| 21. | Feeling worthless. | ⓪ | ① | ② | ③ | ④ | ⑤ |
| 22. | Shortness of breath or rapid heartbeat (not caused by physical exertion). | ⓪ | ① | ② | ③ | ④ | ⑤ |
| 23. | Not enjoying things as much as I used to. | ⓪ | ① | ② | ③ | ④ | ⑤ |
| 24. | Very strong mood swings (highs and lows). | ⓪ | ① | ② | ③ | ④ | ⑤ |
| 25. | Difficulty making decisions. | ⓪ | ① | ② | ③ | ④ | ⑤ |
| 26. | Troubling events in my daily life. | ⓪ | ① | ② | ③ | ④ | ⑤ |
| 27. | Bothered by a fear of something specific. | ⓪ | ① | ② | ③ | ④ | ⑤ |
| 28. | Problems with my health because of my alcohol or drug use. | ⓪ | ① | ② | ③ | ④ | ⑤ |
| 29. | Needing very little sleep. | ⓪ | ① | ② | ③ | ④ | ⑤ |
| 30. | Problems resulting from the loss of an important person or relationship. | ⓪ | ① | ② | ③ | ④ | ⑤ |
| 31. | Feeling tense or anxious. | ⓪ | ① | ② | ③ | ④ | ⑤ |
| 32. | Sleeping too much. | ⓪ | ① | ② | ③ | ④ | ⑤ |
| 33. | Fear of rejection. | ⓪ | ① | ② | ③ | ④ | ⑤ |
| 34. | Feeling that I, or a situation I was in, was not real. | ⓪ | ① | ② | ③ | ④ | ⑤ |
| 35. | Having to avoid certain places or situations because of fearfulness. | ⓪ | ① | ② | ③ | ④ | ⑤ |
| 36. | Worrying too much about unimportant things. | ⓪ | ① | ② | ③ | ④ | ⑤ |
| 37. | Doing things that could have caused trouble for me or my family. | ⓪ | ① | ② | ③ | ④ | ⑤ |
| 38. | Experiencing a great deal of stress. | ⓪ | ① | ② | ③ | ④ | ⑤ |
| 39. | Periods of intense fear that seem out of place or out of proportion. | ⓪ | ① | ② | ③ | ④ | ⑤ |
| 40. | Problems with my family or friends because of my alcohol or drug use. | ⓪ | ① | ② | ③ | ④ | ⑤ |

© Copyright. Integra©, Inc. 1992. All Rights Reserved.

CLINICIAN FORM

GENERAL INFORMATION

PATIENT CODE             __ __ __ __ __ __ __ __ __

THERAPIST CODE           __ __ __ __ __ __ __ __ __

SESSION NUMBER           __ __ __

DATE:                    __/__/__

===================================================

TO BE COMPLETED AFTER INITIAL SESSION ONLY

PATIENT EMPLOYER CODE           __ __ __ __ __

FEE PER SESSION (DOLLARS)       __ __ __

DSM III-R AXIS I DIAGNOSIS CODE    __ __ __.__ __

DSM III-R AXIS II DIAGNOSIS CODE   __ __ __.__ __

===================================================

RATINGS OF PATIENT FUNCTIONING

GLOBAL ASSESSMENT             __ __ __

SELF MANAGEMENT               __ __ __

WORK, SCHOOL, HOUSEHOLD       __ __ __

INTIMATE RELATIONSHIPS        __ __ __

SOCIAL                        __ __ __

FAMILY                        __ __ __

HEALTH AND GROOMING           __ __ __

PATIENT STATUS

1. What is your overall impression of the effect of this treatment?
   THE PATIENT IS:

1. Considerably worse.
   2. Moderately worse.
   3. Slightly worse.
   4. No change.
   5. Slightly improved.
   6. Moderately improved.
   7. Considerably improved.

2. How upset or distressed has your patient been feeling?

1. Extremely distressed.
   2. Very distressed.
   3. Pretty distressed.
   4. Slightly distressed.
   5. Not at all distressed.

3. How much more improvement can realistically be expected if the patient continues in treatment?

1. No more improvement is realistically attainable at this time.
   2. Slightly more improvement.
   3. Moderately more improvement.
   4. Substantially more improvement.

4. How well is your patient getting along, emotionally and psychologically?

1. Quite poorly; can barely manage to deal with things.
   2. Fairly poorly; life is pretty tough for him/her at times.
   3. So-so; manages to keep going with some effort.
   4. Fairly well; has his/her ups and downs.
   5. Quite well; has no important complaints.
   6. Very well; much the way he/she would like to.

APPENDIX "B"

The Howard Outpatient Tracking System

Kenneth I. Howard, Ph.D.
Northwestern University

Robert J. Lueger, Ph.D.
Marquette University

Michael T. O'Mahoney, Ph.D.
Mercy Center for Health Care Services

Peter L. Brill, M.D.
Integra, Inc.

© Copyright by Integra, Inc., 1991
All rights reserved

The Howard Outpatient Tracking System consists of four questionnaires: two Patient Forms and two Clinician Forms. These questionnaires measure the patient's progress in Treatment based on the patient's perspective as well as the clinician's perspective. The instruments are completed periodically throughout the course of treatment, so that the patient's progress can be monitored over time.

From these reports, two separate indexes are derived. The Mental Health Index (MHI) is comprised of scores from three sections in the Patient Forms: Subjective Wellbeing, Current Life Functioning, and Current Symptoms. The Clinical Assessment Index (CAI) is based on ratings in the Clinician Forms: Global Assessment, and the Life Functioning Scales. Scores on both indexes are scaled so that a higher score represents more healthy status and a score of 60 or more indicates that the patient has returned to a normal functional status.

Much of the focus in these questionnaires centers on the patient's functioning in six life areas: family, health, intimacy, social, self-management, and work. These dimensions were selected following a review of other measures of functioning (Green & Gracely, 1987; Dohrenwend, Dohrenwend, Link, & Levav, 1983; Keller, Lavori, Friedman, Nielsen, Endicott, McDonald-Scott, & Andreasen, 1987; Weissman, 1975; World Health Organization, 1988) with the goal of sampling a broad range of relevant life functioning domains.

PATIENT FORMS

There are two Patient Forms: the Patient Initial Form and the Patient Treatment Form. The Patient Initial Form is completed at the beginning of treatment and has three sections in addition to those found in the Patient Treatment Form. One section consists of six demographic questions such as the patient's marital status, educational background, living situation, etc. Another section is an open-ended question asking the patient to describe his/her reasons for seeking psychotherapy. The third section is a 23-item list of presenting problems. The patients rate the extent to which each problem is a reason for his/her seeking psychotherapy. In the presenting problems section, there are at least three questions for each of the six life areas, which is consistent with our other materials. There is also one open-ended response.

---

PRESENTING PROBLEMS

FAMILY FUNCTIONING: reliability = .81
  6. Difficulties getting along with family members (not spouse).
 10. Problems handling family responsibilities.
 22. Difficulties caused by the substance abuse or emotional problems of a member of my family.

HEALTH AND GROOMING: reliability = .42
 16. Feeling distress, anxiety, depression, or anger.
 17. A physical problem, such as illness, pain, or medical symptoms.
 18. Alcohol or drug use.
 19. An eating problem or weight control.

INTIMATE RELATIONSHIPS: reliability = .54
  1. Problems with my spouse or romantic partner.
  2. Difficulty forming or maintaining an intimate relationship.
  3. A sexual problem.

SELF-MANAGEMENT: reliability = .79
 11. Not having a sense of direction or goals in life.
 12. Not managing life well in general.
 13. Low self-esteem.
 14. Not understanding myself.
 15. Reacting too emotionally to events.

SOCIAL RELATIONSHIPS: reliability = .70
  4. Problems getting along with a friend or friends.
  5. An unsatisfying social life.
  8. Feeling comfortable with people in general.

WORK, SCHOOL, OR HOUSEHOLD FUNCTIONING: reliability = .79
  7. Problems getting along with people at work or school.
  9. Not getting things done at work or school.
 20. Problems developing or managing my career.
 21. Missing work or school or not getting there on time.

---

There are four sections which both the Patient Initial Form and the Patient Treatment Form have in common. Both forms contain the three sections which comprise the MHI (Subjective Wellbeing, Current Life Functioning, and Current Symptoms) which has an internal consistency of .81. The other section which is not included in the MHI is a measure of the patient's satisfaction with the six life areas discussed previously. This set provides another assessment of the areas of the patient's life are causing the most problems and how these areas relate to each other. Each item is rated on a ten-point scale.

---

LIFE SATISFACTION

1. At the present time, how satisfied are you with the way you are managing your life (meeting personal goals, self-esteem, self-control)?
2. At the present time, how satisfied are you with your job, progress in school, performance of household activities?
3. At the present time, how satisfied are you with your intimate relationships (spouse, romantic partner)?
4. At the present time, how satisfied are you with your social relationships (friends other than your relatives)?
5. At the present time, how satisfied are you with your family relationships (parents, children, other relatives)?
6. At the present time, how satisfied are you with your health habits (exercise, eating habits)?

---

Subjective wellbeing is related to people's conception of happiness which encompasses a variety of areas. The four items in this section include dimensions of distress, energy and health, emotional and psychological adjustment, and current life satisfaction. This content sampling includes both positive and negative affect (Diener, 1984; Watson & Tellegen, 1985), and health and life satisfaction (Cowen, 1991; Viet & Ware, 1983). Structured responses are provided for each item.

---

SUBJECTIVE WELLBEING
(reliability = .83)

1. At the present time, how well do you feel that you are getting along emotionally and psychologically?
2. At the present time, how energetic and healthy have you been feeling?
3. At the present time, how well do you feel that you are getting along emotionally and psychologically?
4. At the present time, how satisfied have you been feeling with your life?

---

Current Life Functioning Scale. The patient is asked in this section to report to what degree his/her emotional and psychological problems are interfering with his/her life functioning. The 24 items in this scale can be categorized into the six life areas so that there are at least 3 questions per area. The family, intimacy, and social questions inquire about the patient's interactions with others and carrying out his/her responsibilities to these people. The health items address the patient's health habits and hygiene, and the work items refer to the patient's interactions and ability to complete tasks. Self-management items assess the patient's control over, conceptions of, and satisfaction with him/herself.

---

CURRENT LIFE FUNCTIONING
(reliability = .91)

FAMILY FUNCTIONING: reliability = .75
6. My emotional/psychological problems interfere with my interaction with my parents.
7. My emotional/psychological problems interfere with my interaction with my siblings.
10. My emotional/psychological problems interfere with my carrying out family responsibilities.

HEALTH AND GROOMING: reliability = .72
5. My emotional/psychological problems interfere with my ability to maintain my personal appearance.
11. My emotional/psychological problems interfere with my participation in physical activities.
20. My emotional/psychological problems interfere with my maintaining good health habits.

INTIMATE RELATIONSHIPS: reliability = .67
4. My emotional/psychological problems interfere with my interactions with my spouse/romantic partner.
18. My emotional/psychological problems interfere with my ability to form or sustain intimate relationships.
19. My emotional/psychological problems interfere with my enjoyment of sexual activities.

SELF-MANAGEMENT: reliability = .78
13. My emotional/psychological problems interfere with my ability to function as an independent person.
15. My emotional/psychological problems interfere with my ability to manage my finances.
16. My emotional/psychological problems interfere with my planning and enjoying leisure time activities.
17. My emotional/psychological problems interfere with my being the kind of person I would like to be.
21. My emotional/psychological problems interfere with my creative activities.
22. My emotional psychological problems interfere with my ability to control myself and stay out of trouble.

SOCIAL RELATIONSHIPS: reliability = .82
2. My emotional/psychological problems interfere with my interactions with friends.

12. My emotional/psychological problems interfere with my participation in social activities.
24. My emotional/psychological problems interfere with my ability to be comfortable with people.

WORK, SCHOOL, OR HOUSEHOLD FUNCTIONING: reliability = .89
1. My emotional/psychological problems interfere with my ability to perform routine tasks.
3. My emotional/psychological problems interfere with my interactions with people at work.
8. My emotional/psychological problems interfere with my ability to concentrate and complete tasks.
9. My emotional/psychological problems interfere with my performance at work or school.
14. My emotional/psychological problems interfere with my developing or managing my career.
23. My emotional/psychological problems interfere with my attending work or school or getting there on time.

Current Symptom Checklist. Many data collections use a symptom checklist adapted from the SCL-90 (Derogatis, 1977). In the Patient Forms, we have devised a completely new symptom checklist. From clinical diagnoses based on 140 Structured Clinical Interviews for the DSM-III (SCID), we found that 74.3% of the patients had at least one of the following 6 diagnoses: Adjustment Disorder, Anxiety, Bipolar Disorder, Depression, Obsessive-Compulsive Disorder, and Phobia. Of those patients who qualified for any DSM diagnoses, 92.0% had one of these six diagnoses.

Using the Diagnostic and Statistical Manual for Mental Disorders (DSM-III-R), we listed the signs and symptoms for these six diagnoses and also the diagnosis of substance abuse and recast them as a patient self-report symptom checklist. There are at least three questions for each diagnosis; however, the more prevalent the diagnosis was in our original sample, the greater the number of questions pertaining to its area.

CURRENT SYMPTOMS
(reliability = .93)

ADJUSTMENT DISORDER: reliability = .77
5. Headaches.
11. Muscular tension or aches.

12. Feeling blocked at work or school.
19. Feeling ill or rundown.
20. Trouble falling asleep.
26. Troubling events in my daily life.
30. Problems resulting from the loss of an important person or relationship.
37. Doing things that could have caused trouble for me or my family.
38. Experiencing a great deal of stress.

ANXIETY: reliability = .85
4. Avoiding places that seemed too closed in.
15. Being irritable and easily angered.
18. Dizziness.
22. Shortness of breath or rapid heartbeat (not caused by physical exertion).
31. Feeling tense or anxious.
33. Fear of rejection.
34. Feeling that I, or a situation I was in, was not real.
39. Periods of intense fear that seem out of place or out of proportion.

BIPOLAR DISORDER: reliability = .60
3. Thoughts that seemed to race through my mind.
24. Very strong mood swings (highs and lows).
29. Needing very little sleep.

DEPRESSION: reliability = .85
6. Feeling sad most of the day.
9. Being sluggish or lethargic.
10. Thoughts about ending my life.
13. Difficulty concentrating.
14. Feeling hopeless about the future.
21. Feeling worthless.
23. Not enjoying things as much as I used to.
25. Difficulty making decisions.
32. Sleeping too much.

OBSESSIVE-COMPULSIVE DISORDER: reliability = .76
1. Having repetitive thoughts that I cannot get rid of.
7. Trying to push thoughts out of my mind.
17. Engaging in repetitive behaviors to calm myself.
36. Worrying too much about unimportant things.

PHOBIA: reliability = .61
16. Afraid of leaving my home.
27. Bothered by a fear of something specific.
35. Having to avoid certain places or situations because of fearfulness.

SUBSTANCE USE DISORDERS: reliability = .91
2. Problems at work or school because of my alcohol or drug use.
8. Guilt or remorse over my alcohol or drug use.
28. Problems with my health because of my alcohol or drug use.
40. Problems with my family or friends because of my alcohol or drug use.

The Patient Treatment Form which is completed periodically throughout the course of treatment has one section that is not found in the Patient Initial Form. This section focuses on the therapeutic bond (Orlinsky & Howard, 1987) which has three components: working alliance, empathic resonance, and mutual affirmation. Working alliance has to do with the effort the patient and the therapist put into implementing their respective roles. Empathic resonance relates to the patient's perception that the therapist understands him/her, and mutual affirmation pertains to an open, caring regard between the patient and the therapist.

The Patient Treatment Form has nine items taken from the larger 50-item Therapeutic Bond Scale (Saunders, Howard, & Orlinsky, 1989) which is based on the Therapy Session Report (Orlinsky & Howard, 1966). The sum of the nine items correlate .81 with the Therapeutic Bond Scale.

---

THERAPEUTIC BOND
(reliability = .83)

1. How well does your therapist seem to understand what you are feeling and thinking?
2. How helpful do you feel your therapist is?
3. My therapist is attentive to what I try to get across.
4. My therapist is friendly and warm towards me.
5. My therapist seems confident.
6. My therapist seems interested.
7. My therapist seems optimistic.

CLINICIAN FORMS

There are two Clinician Forms. The Clinician Initial Form has one section which is not found in the Clinician Treatment Form. This section consists of an open-ended question asking the therapist to state the patient's reasons for seeking psychotherapy. There is also a place in this section for the therapist to list the patient's diagnoses. Both forms contain one overall rating of the patient along with ratings in six areas of the patient's life functioning. These ratings yield the CAI which has an internal consistency of .84.

The Global Assessment Scale (Endicott, Spitzer, Fleiss, & Cohen, 1976) is a rating of "the patient's lowest level of current functioning" using "a hypothetical continuum of mental health-illness." This scale, which is taken from Axis V of the DSM-III-R, consists of ten 10-point intervals, which correspond to a description of a patient's general functioning, in a 1-100 rating continuum with 100 representing superior status. The clinician is asked to categorize the patient in one of these intervals by providing a specific numerical rating within the range. For example, if the clinician believes the patient belongs in the lowest interval, 1-10, he/she must indicate where in that range the patient falls: 1, 4, 7, etc.

Several studies have assessed the reliability of this measure. Endicott et al. (1976) conducted five studies (on samples which were primarily comprised of inpatients) resulting in test-retest reliabilities ranging from .69 to .91. Clark and Friedman (1983) found the the GAS test-retest reliabilities ranged from .74 to .78 decreasing as the length of time between assessments increased. In a study of chronic outpatients inter-rater reliabilities for the GAS were obtained after four different training sessions involving either previously trained mental health professionals, untrained mental health professionals, or a mixture of trained and untrained clinicians. These interrater reliabilities ranged from .66 to .92 with greater reliabilities associated with the trained clinician groups (Dworkin, Friedman, Telschow, Grant, Moffic, & Sloan, 1990).

GLOBAL ASSESSMENT SCALE

91-100
Superior functioning in a wide range of activities, life's problems never seem to get out of hand, is sought out by others because of his/her warmth and integrity. No symptoms.

81-90
Good functioning in all areas, many interests, socially effective, generally satisfied with life. There may or may not be transient symptoms and "everyday" worries that only occasionally get out of hand.

71-80
No more than slight impairment in functioning, varying degrees of "everyday" worries and problems that sometimes get out of hand. Minimal symptoms may or may not be present.

61-70
Some mild symptoms (e.g., depressive mood, mild insomnia), OR some difficulty in several areas of functioning, but generally functioning pretty well, has some meaningful interpersonal relationships and most untrained people would not consider him/her "sick".

51-60
Moderate symptoms, OR generally functioning with some difficulty (e.g., few friends and flat affect, depressed mood and pathological self-doubt, euphoric mood and pressure of speech, moderately severe antisocial behavior.)

41-50
Any serious symptomatology or impairment in functioning that most clinicians would think obviously requires treatment or attention (e.g., suicidal preoccupation of gesture, severe obsessional rituals, frequent anxiety attacks, serious antisocial behavior, compulsive drinking, mild but definite manic syndrome.)

31-40
Major impairment n several areas, such as work, family relations, judgment, thinking, or mood (e.g., depressed person avoids friends, neglects family, unable to do normal tasks), OR some impairment in reality testing or communication (e.g., speech is at times obscure, illogical, or irrelevant), OR single suicide attempt.

21-30
Unable to function in almost all areas (e.g., stays in bed all day), OR behavior is considerably influenced by either delusions or hallucinations, OR serious impairment in communication (e.g., sometimes incoherent or unresponsive) or judgment (e.g., acts grossly inappropriate).

11-20
Needs some supervision to prevent hurting self or others or to maintain minimal personal hygiene (e.g., repeated suicide attempts, frequently violent, manic excitement, smears feces), OR gross impairment in communication (e.g., largely incoherent or mute).

1-10
Needs constant supervision to prevent hurting self or others, OR makes no attempt to maintain minimal personal hygiene, OR serious suicide act with clear intent and expectation of death.

In addition to the overall rating, the Clinician Report includes six Life Functioning Scales which were devised to separately assess the patient's status in six areas. Each of the six domains of the Life Functioning Scales is rated on a dimension ranging from 0 to 100 with increments of five marking the scale. Five descriptive anchors are common to all scales with each anchor occupying one-fifth of the dimension space. Anchors range from "Severe Impairment, Virtually Unable to Function" on the low end (0-20), to "No Impairment, High Level of Functioning" on the high end (80-100) of the functioning dimension. Five behavioral examples, each of 20 to 50 words are provided with each level to help clarify the labeled levels of functioning. Raters are asked to "circle the number (from 0 to 100) that best applies to this patient's level of [e.g., Family Functioning]."

A preliminary inspection of ratings from therapists on a sample of patients indicated that ratings ranged across the available categories for all six domains. The intercorrelations of the domains ranged from $r = .35$ to $r = .62$. Ratings on the six domains were summed, and alphas were computed. The six-domain alpha was .84. Corrected item-total correlations ranged from .55 to .66. This indicates the presence of an overall dimension of functioning, but indicates meaningful content heterogeneity across the domains. Each of the separate domains and the sum of the six domains of life functioning were correlated with the Global Assessment Scale (GAS). The summed domains correlated .84 with the GAS; the separate domains correlated with the GAS in a range from .34 to .77. This indicates convergence of the underlying dimension with another global measure of functioning.

---

LIFE FUNCTIONING SCALES
(reliability = .84)

SELF-MANAGEMENT
- 100   High self-esteem and self-acceptance; is the kind of person he/she would like to be; manages life extremely well; has a solid sense of direction in life and can identify and is pursuing important goals.
- 80   Generally satisfied with self; is the kind of person he/she would like to be; manages most life areas well; has a sense of direction in life and can identify

| | |
|---|---|
| | important personal goals. |
| 50 | Somewhat satisfied with self but has periods of low self-esteem; would like to improve one or more major areas of self; minor limitations in ability to function independently; somewhat confused about sense of direction in life and important personal goals. |
| 20 | Generally low self-esteem and self-acceptance; seldom satisfied with self; overreacts emotionally; no clear personal goals or direction of life. |
| 0 | Requires continuous guidance or supervision; consistently self-rejecting; no self-control; cannot stay out of trouble. |
| — | No information. |

WORK, SCHOOL, OR HOUSEHOLD FUNCTIONING

| | |
|---|---|
| 100 | Works hard and accomplishes what is called for; maintains excellent work relationships; is developing and managing career effectively. |
| 80 | Works at a satisfactory level; good work relationships; is developing and managing career in a satisfactory manner. |
| 50 | Mild difficulties carrying out work, school, or household activities; some difficulties in work relationships; some difficulties in developing or managing career, misses some work or school. |
| 20 | Has considerable difficulty carrying out work, school, or household activities; significant difficulties in work relationships; career is not developing; misses a lot of work or school or is consistently tardy or neglects household responsibilities. |
| 0 | Virtually unable to carry out any work, school, or household activities; misses a great deal of work or school or totally neglects household responsibilities. |
| — | No information. |

INTIMATE RELATIONSHIPS

| | |
|---|---|
| 100 | Steady relationship with mutual affection, warmth, support, and effective communication; satisfactory sexual relations; conflicts are minor and rapidly resolved. |
| 80 | Steady relationship generally provides affection and support; good communication; occasional conflicts but these are readily resolved; sexual relationship is generally satisfactory to both partners. |
| 50 | Relationship sometimes lacks affection, warmth, and support; sexual relations are less than satisfactory or are somewhat lacking in intimacy. |
| 20 | Lack of support; only rare, occasional expressions of warmth; sexual interest diminished or excessive without regard to mate's feelings, pleasure, etc. |
| 0 | Warmth lacking throughout; no sexual initiative or advances are grossly inappropriate and inconsiderate; risk of physical or sexual violence. |
| — | No information; romantic relationship does not exist due to lifestyle choice (e.g., celibacy) or to other factors (e.g., death of a spouse); or no current relationship and not seeking a relationship. |

SOCIAL FUNCTIONING

| | |
|---|---|
| 100 | Steady; very close friendships with people outside nuclear family; relationships provide consistent warmth and support; frequent contact and no conflicts. |
| 80 | Steady friendships with people outside nuclear family; relationships involve consistent support and at least periodic contact; occasional conflicts are quickly resolved. |
| 50 | Active interest in people outside nuclear family, but contact is sometimes limited by anxiety, sensitivity, or unrealistic expectations; or generally supportive relationships are interrupted by conflicts or withdrawal. |
| 20 | Only occasional interest in people outside nuclear family; relationships lack | support; contact is seldom initiated, or may be periodically avoided; intense conflicts may persist.
0 No interest in people outside nuclear family; severe withdrawal; or hostility/physical assault.
— No information.

FAMILY FUNCTIONING

100 Very close family relationships that include warmth, support, frequent contact, and effective communication; no conflicts.

80 Close family relationships that generally include warmth and support; contact is generally regular, but the quality of communication varies with family members; conflicts are resolved with a minimum of withdrawal.

50 Family relationships are generally supportive but may lack warmth or harmony; contact may be irregular with some members or may lack emotional closeness; conflicts are more frequent and some may have a long resolution time.

20 Family relationships are inconsistently supportive and lack harmony and emotional closeness; some family members may be actively avoided; regular conflicts are rarely resolved.

0 Family relationships are marked by continual conflict; open hostility in the form of physical or sexual abuse may be present; family members regularly withdraw.

— No information; has no living family members.

HEALTH AND GROOMING

100 Enjoys excellent health; regularly and consistently maintains good health habits including regular exercise, proper diet, and abstinence from health hazards (e.g., smoking, excessive alcohol use).

80 Generally enjoys good health with occasional minor illness; generally maintains good health habits including exercise, proper diet, and abstinence from health hazards.

50 Generally enjoys good health, but has some limitations in physical activities; or lapses in health habits such as a lack of physical exercise, or excessive weight, or engagement in behaviors hazardous to health (e.g., smoking, regular heavy drinking).

20 Generally in poor health; limitations in several areas of physical activity or recovering from a physical condition; an extended lapse in health habits such as rare physical exercise, grossly overweight, regular heavy smoking, or daily heavy drinking.

0 Disabled or bedridden; unable to perform routine or regular vocational or household activities; confined to bed or hospital care.

— No information.

References

Carter, D.E., & Newman, F.L. (1980). <u>A client-oriented system of mental health service delivery and program management: A workbook and guide</u>. National Institute of Mental Health, Series FN No.4. DHHS Publication No. (ADN) 80-307. Washington, D.C.: U.S. Government Printing Office.

Clark, A., & Friedman, M.J. (1983). Nine standardized scales for evaluating treatment outcome in a mental health clinic. <u>Journal of Clinical Psychology, 39</u>(6), 939-950.

Cowen, E.L. (1991). In pursuit of wellness. <u>American Psychologist, 46</u>, 404-408.

Diener, E. (1984). Subjective well-being. <u>Psychological Bulletin, 95</u>(3), 542-575.

Derogatis, L.R. (1977). <u>SCL-90: Administration and Procedures Manual-I for the R(evised) Version</u>. Baltimore: Clinical Psychometrics Research.

Dohrenwend, B.S., Dohrenwend, B.P., Link, B., & Levav, I. (1983). Social functioning of psychiatric patients in contrast with community cases in the general population. <u>Archives of General Psychiatry, 40</u>, 1174-1182.

Dworkin, R.J., Friedman, L.C., Telschow, R.L., Grant, K.D., Moffic, H.S., & Sloan, V.J. (1990). The longitudinal use of the Global Assessment Scale in multiple-rater situations. <u>Community Mental Health Journal, 26</u>(4), 335-344.

Endicott, J., Spitzer, R.L., Fleiss, J.L., & Cohen, J. (1976). The Global Assessment Scale: A procedure for measuring overall severity of psychiatric disturbance. <u>Archives of General Psychiatry, 33</u>, 766-771.

Green, R.S., & Gracely, E.J. (1987). Selecting a rating scale for evaluating services to the chronically mentally ill. <u>Community Mental Health Journal, 23</u>, 91-102.

Keller, M.B., Lavori, P.W., Friedman, B., Nielsen, E., Endicott, J., McDonald-Scott, P., & Andreasen, N.C. (1987). The longitudinal interval follow-up evaluation. <u>Archives of General Psychiatry, 44</u>, 540-548.

Orlinsky, D.E., & Howard, K.I. (1966). <u>Psychotherapy Session Report, Form P</u>. Chicago: Institute of Juvenile Research.

Orlinsky, D.E., & Howard, K.I. (1986). A generic model of psychotherapy. *Journal of Integrative and Eclectic Psychotherapy, 6,* 6-27.

Saunders, S.M., Howard, K.I., & Orlinsky, D.E. (1989). The Therapeutic Bond Scales: Psychometric characteristics and relationship to treatment effectiveness. *Psychological Assessment, 1*(4), 323-330.

Viet, C.T., & Ware, Jr., J.E. (1983). The structure of psychological distress and well-being in general populations. *Journal of Consulting and Clinical Psychology, 51,* 730-742.

Watson, D., & Tellegen, A. (1985). Toward a consensual structure of mood. *Psychological Bulletin, 98,* 219-235.

Weissman, M.M. (1975). The assessment of social adjustment. *Archives of General Psychiatry, 32,* 357-365.

World Health Organization. (1988). *WHO Psychiatric Disability Assessment Schedule (WHO/DAS) with a guide to its use.* Geneva: World Health Organization.